(12) United States Patent
Manash et al.

(10) Patent No.: US 11,877,925 B2
(45) Date of Patent: *Jan. 23, 2024

(54) SYSTEMS AND MECHANISMS FOR DEPLOYING A DOCKING DEVICE FOR A REPLACEMENT HEART VALVE

(71) Applicant: Edwards Lifesciences Corporation, Irvine, CA (US)

(72) Inventors: Boaz Manash, Givat Ada (IL); Yoav Rozen, Binyamina (IL); Eitan Atias, Tel Aviv (IL)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 234 days.

This patent is subject to a terminal disclaimer.

(21) Appl. No.: 17/037,451

(22) Filed: Sep. 29, 2020

(65) Prior Publication Data
US 2021/0007842 A1 Jan. 14, 2021

Related U.S. Application Data

(63) Continuation of application No. 15/984,678, filed on May 21, 2018, now Pat. No. 11,065,111, which is a (Continued)

(51) Int. Cl.
*A61F 2/24* (2006.01)

(52) U.S. Cl.
CPC .............. *A61F 2/2409* (2013.01); *A61F 2/24* (2013.01); *A61F 2/2427* (2013.01); (Continued)

(58) Field of Classification Search
CPC ........ A61F 2/24; A61F 2/2409; A61F 2/2427; A61F 2/2436; A61F 2/2439
See application file for complete search history.

(56) References Cited

U.S. PATENT DOCUMENTS 4,035,849 A 7/1977 Angell et al.
4,592,340 A 6/1986 Boyles
(Continued)

FOREIGN PATENT DOCUMENTS

CN 102639179 A 8/2012
CN 104220027 A 12/2014
(Continued)

*Primary Examiner* — Tuan V Nguyen
(74) *Attorney, Agent, or Firm* — Edwards Lifesciences; Linda Allyson Nassif

(57) ABSTRACT

Systems and methods usable in delivering a docking device to a native valve of a patient's heart. A distal region of a delivery catheter can be positioned in an atrium of the heart and a distal tip can be positioned at or near a commissure of the native valve. The docking device can be located within the delivery catheter. A pusher, such as a pusher wire or tube, of a pusher tool can be advanced distally through the delivery catheter, wherein the pusher can push the docking device along within the delivery catheter. The docking device can be connected to the pusher tool by a line, such as a suture. A member of the pusher tool can be rotatable to change the amount of the suture extending from the pusher tool.

24 Claims, 20 Drawing Sheets

Related U.S. Application Data continuation of application No. PCT/US2017/066865, filed on Dec. 15, 2017.

(60) Provisional application No. 62/560,962, filed on Sep. 20, 2017, provisional application No. 62/436,695, filed on Dec. 20, 2016.

(52) U.S. Cl.
CPC ..... *A61F 2/2418* (2013.01); *A61F 2220/0033* (2013.01); *A61F 2230/0091* (2013.01); *A61F 2250/0063* (2013.01)

(56) References Cited

U.S. PATENT DOCUMENTS

| | | |
|---|---|---|
| 4,994,077 A | 2/1991 | Dobben |
| 5,059,177 A | 10/1991 | Towne et al. |
| 5,327,905 A | 7/1994 | Avitall |
| 5,350,397 A | 9/1994 | Palermo et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,639,274 A | 6/1997 | Fischell et al. |
| 5,728,068 A | 3/1998 | Leone et al. |
| 5,840,081 A | 11/1998 | Andersen et al. |
| 5,968,068 A | 10/1999 | Dehdashtian et al. |
| 6,168,614 B1 | 1/2001 | Andersen et al. |
| 6,217,585 B1 | 4/2001 | Houser et al. |
| 6,379,372 B1 | 4/2002 | Dehdashtian et al. |
| 6,419,696 B1 | 7/2002 | Ortiz et al. |
| 6,432,134 B1 | 8/2002 | Anson et al. |
| 6,454,799 B1 | 9/2002 | Schreck |
| 6,458,153 B1 | 10/2002 | Bailey et al. |
| 6,461,382 B1 | 10/2002 | Cao |
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,767,362 B2 | 7/2004 | Schreck |
| 6,797,002 B2 | 9/2004 | Spence et al. |
| 6,830,584 B1 | 12/2004 | Seguin |
| 6,893,460 B2 | 5/2005 | Spenser et al. |
| 6,908,481 B2 | 6/2005 | Cribier |
| 7,004,176 B2 | 2/2006 | Lau |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,226,467 B2 | 6/2007 | Lucatero et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,708,775 B2 | 5/2010 | Rowe et al. |
| 7,737,060 B2 | 6/2010 | Strickler et al. |
| 7,785,366 B2 | 8/2010 | Maurer et al. |
| 7,951,195 B2 | 5/2011 | Antonsson et al. |
| 7,959,661 B2 | 6/2011 | Hijlkema et al. |
| 8,029,556 B2 | 10/2011 | Rowe |
| 8,128,691 B2 | 3/2012 | Keranen |
| 8,167,932 B2 | 5/2012 | Bourang et al. |
| 8,236,049 B2 | 8/2012 | Rowe et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,454,683 B2 | 6/2013 | Rafiee et al. |
| 8,652,202 B2 | 2/2014 | Alon et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 9,078,747 B2 | 7/2015 | Conklin |
| 9,095,434 B2 | 8/2015 | Rowe |
| 9,119,718 B2 | 9/2015 | Keranen |
| 9,237,886 B2 | 1/2016 | Seguin et al. |
| 9,364,326 B2 | 6/2016 | Yaron |
| 9,463,268 B2 | 10/2016 | Spence |
| 9,474,599 B2 | 10/2016 | Keranen |
| 9,597,205 B2 | 3/2017 | Tuval |
| 9,622,863 B2 | 4/2017 | Karapetian et al. |
| 9,867,702 B2 | 1/2018 | Keränen et al. |
| 10,195,033 B2 | 2/2019 | Tuval et al. |
| 11,020,225 B2 | 6/2021 | Keränen et al. |
| 11,039,924 B2 | 6/2021 | Yaron |
| 11,364,114 B2 | 6/2022 | Gorman, III et al. |
| 2002/0032481 A1 | 3/2002 | Gabbay |
| 2002/0107535 A1 | 8/2002 | Wei et al. |
| 2003/0050694 A1 | 3/2003 | Yang et al. |
| 2003/0074045 A1 | 4/2003 | Buzzard et al. |
| 2003/0105520 A1 | 6/2003 | Alferness et al. |
| 2003/0225420 A1 | 12/2003 | Wardle |
| 2004/0111006 A1 | 6/2004 | Alferness et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137691 A1 | 6/2005 | Salahieh et al. |
| 2005/0149160 A1 | 7/2005 | McFerran |
| 2005/0182486 A1 | 8/2005 | Gabbay |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2007/0005131 A1 | 1/2007 | Taylor |
| 2007/0203575 A1 | 8/2007 | Forster et al. |
| 2007/0265700 A1 | 11/2007 | Eliasen et al. |
| 2007/0293808 A1 | 12/2007 | Williams et al. |
| 2008/0033542 A1 | 2/2008 | Antonsson et al. |
| 2008/0077235 A1 | 3/2008 | Kirson |
| 2008/0097398 A1 | 4/2008 | Mitelberg et al. |
| 2008/0125853 A1 | 5/2008 | Bailey et al. |
| 2008/0208330 A1 | 8/2008 | Keranen |
| 2008/0228267 A1* | 9/2008 | Spence .............. A61B 17/0487 623/2.36 |
| 2008/0294230 A1 | 11/2008 | Parker |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0145440 A1 | 6/2010 | Keranen |
| 2010/0198347 A1 | 8/2010 | Zakay et al. |
| 2010/0312333 A1 | 12/2010 | Navia et al. |
| 2010/0318184 A1 | 12/2010 | Spence |
| 2011/0015729 A1 | 1/2011 | Jimenez et al. |
| 2012/0059458 A1 | 3/2012 | Buchbinder et al. |
| 2012/0123529 A1 | 5/2012 | Levi et al. |
| 2012/0283820 A1 | 11/2012 | Tseng et al. |
| 2013/0317598 A1 | 11/2013 | Rowe et al. |
| 2014/0074299 A1 | 3/2014 | Endou et al. |
| 2014/0081394 A1 | 3/2014 | Keranen et al. |
| 2014/0172070 A1 | 6/2014 | Seguin |
| 2014/0358222 A1 | 12/2014 | Gorman, III et al. |
| 2014/0379074 A1 | 12/2014 | Spence et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |

(56) References Cited

U.S. PATENT DOCUMENTS

| | | |
|---|---|---|
| 2015/0374493 A1 | 12/2015 | Yaron et al. |
| 2016/0074165 A1 | 3/2016 | Spence et al. |
| 2016/0095705 A1 | 4/2016 | Keranen et al. |
| 2016/0184095 A1 | 6/2016 | Spence et al. |
| 2016/0199177 A1 | 7/2016 | Spence et al. |
| 2016/0228247 A1 | 8/2016 | Maimon et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2018/0206074 A1 | 7/2018 | Tanasa et al. |

FOREIGN PATENT DOCUMENTS

| | | |
|---|---|---|
| DE | 19532846 A1 | 3/1997 |
| DE | 19907646 A1 | 8/2000 |
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| EP | 3395296 B1 | 12/2019 |
| EP | 2747708 B1 | 1/2022 |
| FR | 2815844 A1 | 5/2002 |
| FR | 2915087 A1 | 10/2008 |
| WO | 9117720 A1 | 11/1991 |
| WO | 9829057 A1 | 7/1998 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03028558 A2 | 4/2003 |
| WO | 03047468 A1 | 6/2003 |
| WO | 2005084595 A1 | 9/2005 |
| WO | 2006011127 A2 | 2/2006 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2008112740 A2 | 9/2008 |
| WO | 2009155561 A2 | 12/2009 |
| WO | 2010121076 A2 | 10/2010 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016090025 A1 | 6/2016 |
| WO | 2016130820 A1 | 8/2016 |
| WO | 2017103833 A1 | 6/2017 |

* cited by examiner

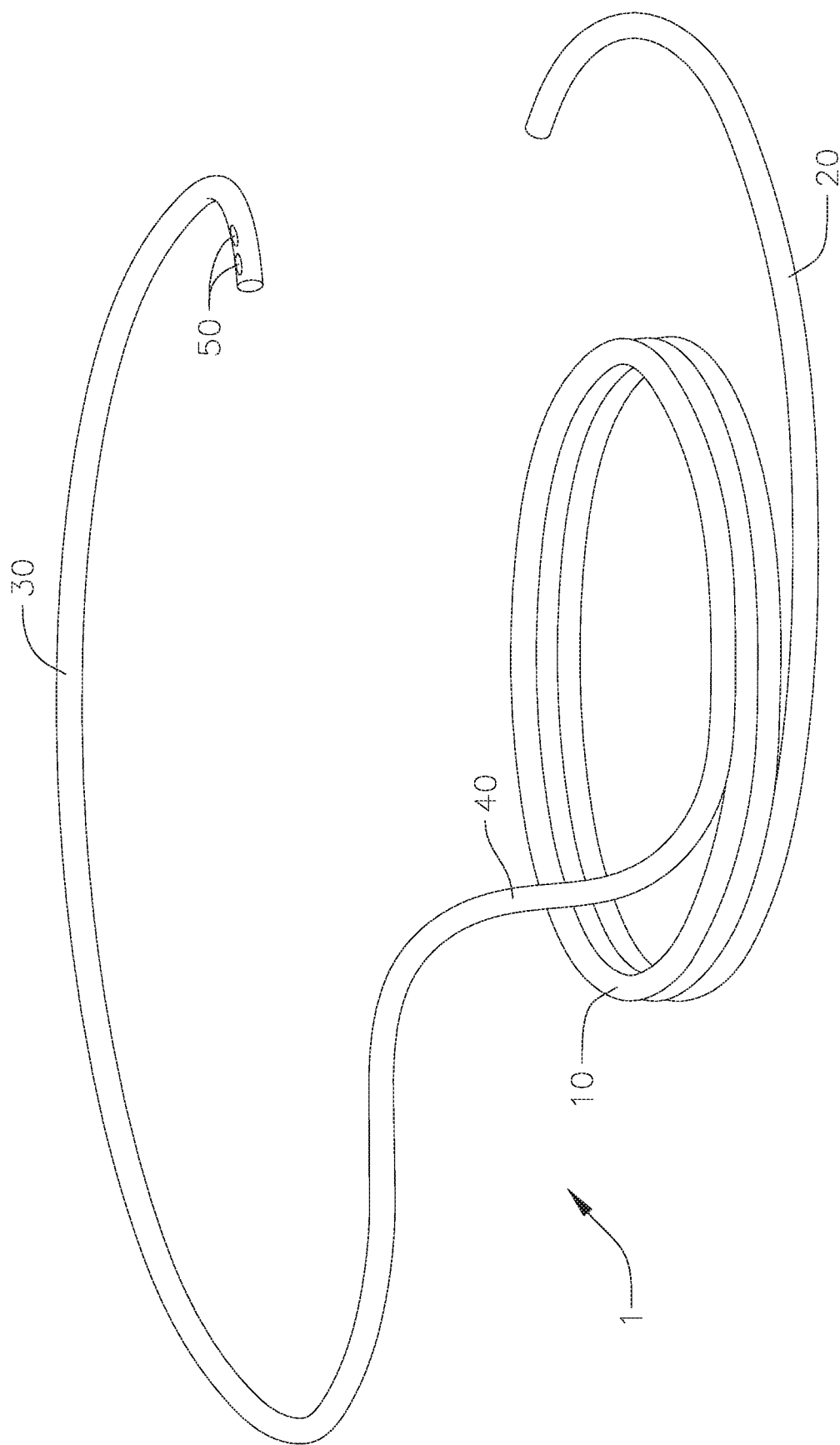

SYSTEMS AND MECHANISMS FOR DEPLOYING A DOCKING DEVICE FOR A REPLACEMENT HEART VALVE

RELATED APPLICATIONS

The present application is a continuation of U.S. patent application Ser. No. 15/984,678, filed May 21, 2018, which is a continuation of PCT Patent Application Serial No. PCT/US2017/066865 titled "SYSTEMS AND MECHANISMS FOR DEPLOYING A DOCKING DEVICE FOR A REPLACEMENT HEART VALVE" filed on Dec. 15, 2017, which claims the benefit of U.S. Provisional Patent Application Ser. No. 62/436,695, filed on Dec. 20, 2016 and U.S. Provisional Patent Application Ser. No. 62/560,962, filed on Sep. 20, 2017. The entire disclosures of these applications are incorporated herein by reference in their entirety.

FIELD

The present disclosure generally relates to medical devices and procedures pertaining to prosthetic heart valves which replace the functionality of native valves that may have malformations and/or dysfunctions and associated devices, such as anchoring or docking devices.

BACKGROUND

Referring first to FIGS. 1 and 2, the mitral valve 51 controls the flow of blood between the left atrium 52 and the left ventricle 54 of the human heart and, similarly, the tricuspid valve 53 controls the flow of blood between the right atrium and the right ventricle. For example, after the left atrium 52 receives oxygenated blood from the lungs via the pulmonary veins, the mitral valve 51 permits the flow of the oxygenated blood from the left atrium 52 into the left ventricle 54. When the left ventricle 54 contracts, the oxygenated blood that was held in the left ventricle 54 is delivered through the aortic valve 56 and the aorta 58 to the rest of the body. Meanwhile, the mitral valve should close during ventricular contraction to prevent any blood from flowing back into the left atrium.

When the left ventricle contracts, the blood pressure in the left ventricle increases substantially, which serves to urge the mitral valve closed. Due to the large pressure differential between the left ventricle and the left atrium during this time, a large amount of pressure is placed on the mitral valve, leading to a possibility of prolapse, or eversion of the leaflets of the mitral valve back into the atrium. A series of chordae tendineae 62 therefore connect the leaflets of the mitral valve to papillary muscles located on the walls of the left ventricle, where both the chordae tendineae and the papillary muscles are tensioned during ventricular contraction to hold the leaflets in the closed position and to inhibit them from extending back towards the left atrium. This helps prevent backflow of oxygenated blood back into the left atrium. The chordae tendineae 62 are schematically illustrated in both the heart cross-section of FIG. 1 and the top view of the mitral valve of FIG. 2.

A general shape of the mitral valve and its leaflets as viewed from the left atrium is shown in FIG. 2. Commissures 64 are located at the ends of the mitral valve 51 where the anterior leaflet 66 and the posterior leaflet 68 come together. Various complications of the mitral valve can potentially cause physical problems, including fatal heart failure. One form of valvular heart disease is mitral valve leak or mitral regurgitation, characterized by abnormal leaking of blood from the left ventricle through the mitral valve back into the left atrium. This can be caused, for example, by dilation of the left ventricle and/or mitral valve annulus causing the native mitral leaflets not to coapt completely, resulting in a leak or regurgitation. This can also lead to problems with the native leaflets, and/or weakening of (or other problems with) the chordae tendineae and/or papillary muscles, which can in turn lead to mitral regurgitation. In these circumstances, it may be desirable to repair the mitral valve or to replace the functionality of the mitral valve with that of a prosthetic heart valve.

However, there has been limited research devoted to developing commercially available ways to replace a mitral valve through catheter implantation and/or other minimal or less invasive procedures, instead of via open-heart procedures. This may stem from mitral valve replacement being more difficult than aortic valve replacement in respects not accounted for by aortic valve replacement technology, for example, due to the non-circular physical structure of and more difficult access to the mitral annulus. Since transcatheter aortic valve technology is more developed, it could be beneficial to adapt similar circular valve prostheses for mitral applications.

A prominent obstacle for mitral valve replacement is effective anchoring or retention of the valve at the mitral position, due to the valve being subject to a large cyclic load. Especially during ventricular contraction, the movement of the heart and the load or pressure on the valve can combine to shift or dislodge an inadequately anchored prosthetic valve. In addition, the movement and rhythmic load can easily fatigue the implant, leading to fractures or other damage to the implant. Even a slight shift in the alignment of the valve may lead to the blood flow through the valve being negatively affected. Meanwhile, puncturing the tissue in or around the mitral valve annulus to better anchor the implanted valve can lead to unintended perforation of the heart and patient injury.

Another issue with mitral and tricuspid valve replacement is the size and shape of the native annulus. For example, a circular or cylindrical replacement valve similar to replacement aortic valves may not fit the mitral position. A replacement valve that is too small or the wrong shape may cause leaks around the implanted valve (i.e., paravalvular leak), if a good seal is not established around the valve. A replacement valve that is too large may stretch out and damage the native annulus. Furthermore, the presence of the chordae tendineae and other anatomy can form obstructions that make it more challenging to adequately anchor a device at the mitral position. Also, significant variations in anatomy of a mitral and/or tricuspid valve from patient to patient make it difficult to have a solution that will work for all or at least a wide variety of patients.

SUMMARY

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure may be included in the examples summarized here.

One way to apply circular or cylindrical transcatheter valve technology (e.g., as may be used with aortic valve replacement) to non-circular valve replacement (e.g., mitral valve replacement, tricuspid valve replacement, etc.) would be to use an anchor (e.g., a coiled anchor, helical anchor, mitral anchor, etc.) or docking device/docking station that forms or otherwise provides a more circular or cylindrical docking site at the native valve position (e.g., mitral valve position) to hold such prosthetic valves.

The anchoring or docking devices themselves can be designed for delivery via a transcatheter approach. One such anchoring or docking device is a coil or anchor that includes a helically shaped region that has a plurality of turns defining a circular or cylindrical inner space for docking the prosthesis or bioprosthesis, e.g., THV. In this manner, existing expandable transcatheter valves developed for the aortic position, or similar valves that have been slightly modified to more effectively replicate native valve function (e.g., native mitral valve function), could be more securely implanted in such a docking device/station positioned at the native valve annulus (e.g., native mitral annulus).

The docking device/station can first be positioned at the native valve annulus, and thereafter, the prosthesis (e.g., valve implant or transcatheter heart valve) can be advanced and positioned through the docking device/station while in a collapsed position, and can then be expanded, for example, via self-expansion (e.g., in the case of valves that are constructed with NiTi or another shape memory material), balloon expansion, or mechanical expansion, so that the frame of the prosthetic valve pushes radially against the docking device/station and/or tissue between the two to hold the valve in place.

Preferably, the docking device/station can also be delivered minimally or less invasively, for example, via the same or similar approaches (e.g., transcatheter approaches) as used for delivery of a prosthetic valve (e.g., a transcatheter heart valve), so that a completely separate procedure is not needed to implant the docking device/station prior to delivery of the prosthetic valve. Such docking devices can also potentially be used at any of the heart's native valves, for example, at the tricuspid, pulmonary, or aortic positions, to provide more secure implantation of prosthetic valves at those sites as well.

Deployment tools can be used to deliver these anchors or anchoring devices (e.g., coiled or helical anchoring devices) to an implant site prior to delivery of the THV, to provide a more stable foundation or support structure into or against which the THV can be expanded or otherwise implanted. For example, a guide sheath and/or delivery catheter can be advanced through a patient's vasculature, so that a distal end of the delivery catheter is positioned at or near the implant site. The anchor or docking device can then be advanced through and/or out of the delivery catheter and transitioned and/or adjusted to a desired shape and position at the implant site. Optionally, a shape of the distal region of the delivery catheter can also be bent, angled, or otherwise adjusted to facilitate easier or more proper positioning of the anchor or docking device at the implant site. A handle of the delivery catheter can be designed to allow a practitioner or other end user to easily control the shape and/or movements of the distal region of the delivery catheter.

An advancement tool or mechanism (e.g., a pusher tool) can be part of a system for delivering the anchoring or docking device and can be used to physically push or otherwise advance the anchoring or docking device through and/or out of the delivery catheter. Pusher tools or other pushing mechanisms that provide an easy and effective way to advance an anchoring device through a delivery catheter to an implant site are described. Optionally, the pusher tool can also facilitate retraction and/or retrieval of the helical anchor back into the delivery catheter, for example, to reposition or remove the anchoring/docking device.

Delivery devices and systems for delivering a coiled anchoring device to a native valve annulus of a patient's heart can include various features, including those described in various locations in this disclosure. The anchoring device can be configured to secure a prosthetic heart valve at the native valve annulus. The delivery devices and systems can include a delivery catheter having a longitudinal axis and a distal region configured or adjustable/transitionable to curve in a plane (e.g., in a plane that intersects the longitudinal axis).

The delivery devices and systems can also include a pusher tool. The pusher tool can have a pusher (e.g., comprising a pusher wire, pusher tube, etc.) connectable (indirectly or directly) to the delivery catheter on a side opposite the distal region of the delivery catheter. For example, the delivery catheter can include a handle or be attached/connected to a handle that is connected or connectable to the pusher tool and/or pusher. Optionally, the pusher tool and/or pusher does not need to connect directly or fixedly to the catheter handle or delivery catheter, but can merely have the pusher or pusher wire inserted therethrough.

The pusher tool can include a body and a pusher. The body can be configured to be rotationally fixed relative to the delivery catheter or be configured such that the pusher tool and/or pusher can be fixed or locked (e.g., to a stabilizer) such that the pusher tool and/does not rotate relative to the delivery catheter. The pusher tool can include a control (e.g., knob, button, tab, input, etc.) connected to the body and/or a pusher (e.g., a pusher wire or tube). In one embodiment, the control is a knob rotatable relative to the body, and the pusher is connected to the knob. The pusher (e.g., pusher wire or pusher tube) can be configured to extend through the body to the delivery catheter, and to move translationally and/or axially in the delivery catheter when the control is actuated (e.g., when the knob is rotated relative to the body) to move an anchoring device that is held in the delivery catheter.

Methods of delivering a docking device or anchoring device (e.g., a helical or coiled anchoring device) to a native valve of a patient's heart can include a variety of steps, including steps disclosed in various locations in this disclosure. For example, the methods can include obtaining and/or providing an anchoring device/docking device (e.g., a coiled or helical anchoring device), a delivery catheter, a guide sheath, a pusher tool and/or pusher, and/or various systems, devices, and/or other components. The anchoring device can be configured to secure a prosthetic heart valve at the native valve.

In one embodiment, the methods include positioning a distal region of a delivery catheter in an atrium of the heart, adjusting or transitioning the delivery catheter to a first position and/or configuration where the distal region of the delivery catheter curves at least partially around the native valve and/or positioning a distal opening of the delivery catheter at or near a commissure of the native valve.

A pusher or pusher wire/tube is used to push all or part, such as a first portion (e.g., an encircling turn/coil and functional turns/coils), of the anchoring device out of the distal opening of the delivery catheter and into a ventricle of the heart. This can be done while holding the delivery catheter at the first position. The guide sheath, delivery catheter, pusher tool/pusher can be fixed or held in position at a proximal end by locking or securing the proximal end or a handle/body at the proximal end in a stabilizer (e.g., a stabilization device).

Where the pusher or pusher wire/tube includes a pusher tool having a knob (or other control) that can move and/or control the pusher or pusher wire/tube, the methods include rotating the knob (or otherwise actuating a control) of the pusher tool in a first direction to advance the pusher or pusher wire/tube distally through the delivery catheter while the delivery catheter is held at the first position. As the knob is rotated (or control is actuated) and the pusher or pusher wire/tube is advanced distally, the pusher or pusher wire/tube can push all or part, such as a first portion (e.g., an encircling turn/coil and functional turns/coils), of the anchoring device out of the distal opening of the delivery catheter and into the ventricle. This can include pushing the anchoring device through the commissure of the native valve, if the distal opening is positioned on the atrial side of the commissure.

Where the previous step only involves using the pusher or pusher tube/wire to push a first portion out of the distal end of the catheter (e.g., while the delivery catheter is held stationary), the methods then involve releasing a second portion (e.g., a stabilization coil/turn or atrial coil/turn) of the anchoring device from the delivery catheter. This can be done in a variety of ways. For example, the pusher tool, pusher, and/or pusher wire/tube can be locked or fixed in position (e.g., by locking or fixing a proximal end thereof, such as in a stabilizer, and/or by locking/holding/maintaining the knob in position), while the delivery catheter is pulled or retracted proximally. This can hold the anchoring device in position (e.g., because it abuts the stationary pusher or pusher wire/tube) while unsheathing it from the delivery catheter. If a guide sheath is used, the guide sheath can also be locked/fixed in position (e.g., in the stabilizer) while the delivery catheter is retracted.

Optionally, if the system is so configured, rotating a body of the pusher in a direction opposite to the first direction while holding a position of the knob (e.g., wherein the body of the pusher and the delivery catheter are rotationally fixed relative to one another such that the knob holds a position of the anchoring device at the native valve while the rotation of the body also rotates the distal region of the delivery catheter) causes proximal movement of the delivery catheter to release the second portion of the anchoring device from the distal opening of the delivery catheter into the atrium.

In one embodiment, delivery devices and systems for delivering an anchoring or docking device to a native valve annulus of a patient's heart comprise a delivery catheter and a pusher tool. The delivery catheter has at least one lumen (e.g., a first lumen) and can have multiple lumens, e.g., 2-6 lumens. The pusher tool comprises a pusher or pusher wire or tube. The pusher tool can also include a suture or line (e.g., a connecting or retrieval suture/line) and/or a suture or line lock or locking mechanism. The pusher tool can also include a rotatable member. The pusher or pusher wire or tube is slidably received within the first lumen. The pusher or pusher wire or tube has a distal portion and a proximal portion, and can have a lumen (e.g., a pusher lumen or second lumen) extending from the proximal portion to the distal portion.

The suture or line lock or locking mechanism can have any of the features/components described in various locations in this disclosure. For example, the suture/line lock or locking mechanism can be attached to the proximal portion of the pusher or pusher wire or tube. The suture or line (e.g., retrieval suture or line) can extend through the lumen (e.g., pusher lumen/second lumen) from the suture or line lock or locking mechanism to the docking device to connect the anchoring or docking device to the pusher tool.

The suture/line lock or locking mechanism can include a rotatable member connected to the suture or line (e.g., the retrieval suture or line). The rotatable member can be lockable in position in a variety of ways, for example, the rotatable member can have a first position (e.g., a locked or non-rotational position) that locks the amount of suture or line (e.g., the retrieval suture or line) that extends from the lock or locking mechanism and can have a second position (e.g., a movable or rotational position) that allows the amount of retrieval suture or line that extends from the lock or locking mechanism to be increased or decreased.

Methods of delivering an anchoring or docking device to a native valve of a patient's heart can include additional steps. For example, a distal region of a delivery catheter can be positioned in an atrium of the heart. The anchoring/docking device can be positioned or located within the delivery catheter. A pusher (e.g., a pusher wire or tube) of a pusher tool can be advanced distally through the delivery catheter, such that the pusher pushes and/or pulls the anchoring/docking device within and/or into or out of the delivery catheter (e.g., the pusher tool can be used to push the anchoring/docking device axially or distally within and/or out of the delivery catheter, and the pusher tool can be used to pull/retract the anchoring/docking device axially or proximally into and/or within the delivery catheter). The docking device can be connected to the pusher tool by a connector, e.g., a suture or line (e.g., optionally, using a suture/line lock or locking mechanism the same as or similar to those described in various locations in this disclosure). A member (e.g., a rotatable member) of the pusher tool can be rotated to change the amount of the suture extending from the pusher tool.

A replacement valve, for example, at the mitral or tricuspid position, can be held more securely through the use of a separate anchoring/docking device that provides a more stable docking site for the replacement valve. The anchoring/docking device is delivered through a delivery catheter, and a pusher tool or other pushing mechanism is used to provide easier control in advancing, retracting, positioning, and/or repositioning of the anchoring device at the implant site. The pusher tool can include a pusher, such as a pusher wire or pusher tube.

A pusher or pusher wire/pusher tube can be configured to extend through any of the delivery catheters disclosed herein. The pusher wire/tube can have a plurality of sections, and each of the plurality of sections can have a different stiffness. A first section of the of the pusher wire/tube can have a first stiffness, a second section of the pusher wire/tube can have a second stiffness, and a third section of the pusher wire/tube can have a third stiffness. The stiffness of the first section can be less than the stiffness of the second section, which can be less than the stiffness of the third section. The pusher wire/tube can be constructed of hypotube, polymer tube, coil pipe, coil spring, flexible tube, wire, rod, etc. One or more sections (e.g., the third section) of a pusher tube can be constructed of an uncut hypotube. One or more sections (e.g., the first section, second section, and/or third section) of a pusher tube can be constructed of a hypotube having interrupted cuts. The frequency and/or size of the interrupted cuts can change along the length of the hypotube. The pusher wire/tube can further include a cover (e.g., a polymer cover, fabric cover, etc.).

In one embodiment, the pusher tool includes a distal portion and a proximal portion, a lumen extending from the proximal portion to the distal portion, and an opening at the distal portion. A line or suture (e.g., a retrieval line/suture) extends through the lumen to connect the pusher tool to a proximal end of a docking device. The line/suture (e.g., retrieval line) can be threaded through a hole near the proximal end of the docking device thereby connecting the docking device to the pusher tool. The line/suture (e.g., retrieval line) can be threaded from the distal end of the pusher tool back through the central lumen to a proximal region of the pusher tool. First and second ends of the retrieval line can be connected to the proximal portion of the pusher tool. The pusher tool can further include a pusher or pusher wire/tube. The pusher or pusher wire/tube can have a distal end comprising a braided layer. The pusher tool can have a pusher or pusher wire/tube that includes a distal end having a soft layer. The pusher tool can further have a pusher or pusher wire/tube that includes a distal end having a rounded or curved tip region.

The pusher tool can further comprise a suture or line lock or locking mechanism, which can have any of the features/components described in various locations in this disclosure. In one embodiment, the lock or locking mechanism includes a body having a first portion, a second portion extending away from a central region of the first portion, and a rotatable member connected to and rotatable relative to the first portion of the body. The lock or locking mechanism can further include a handle at a first end of the body that extends from a side of the first portion of the body. The handle can facilitate turning the rotatable member relative to the first portion of the body. The lock or locking mechanism further includes an engagement feature at a second end of the body opposite the handle, wherein the engagement feature connects at least one end of the line/suture to the body. The lock or locking mechanism can further include a bore extending through the second portion of the body and connecting the first portion of the body with a distal opening of the body. The bore creates a pathway from the second portion of the body to the first portion of the body, wherein the pathway can allow the line to engage the rotatable member. The line/suture is anchorable using the engagement feature. Rotating the handle can be used to adjust an amount of the line that is wound around the rotatable member. The lock or locking mechanism can further include a window in the second portion that exposes a portion of the line. The lock or locking mechanism can further include a seal cap connected to the second portion of the body.

BRIEF DESCRIPTION OF THE DRAWINGS

Further features and advantages of the invention will become apparent from the description of embodiments using the accompanying drawings. In the drawings:

FIG. 3 shows a perspective view of an exemplary helical anchoring or docking device;

DETAILED DESCRIPTION

Figure 1:
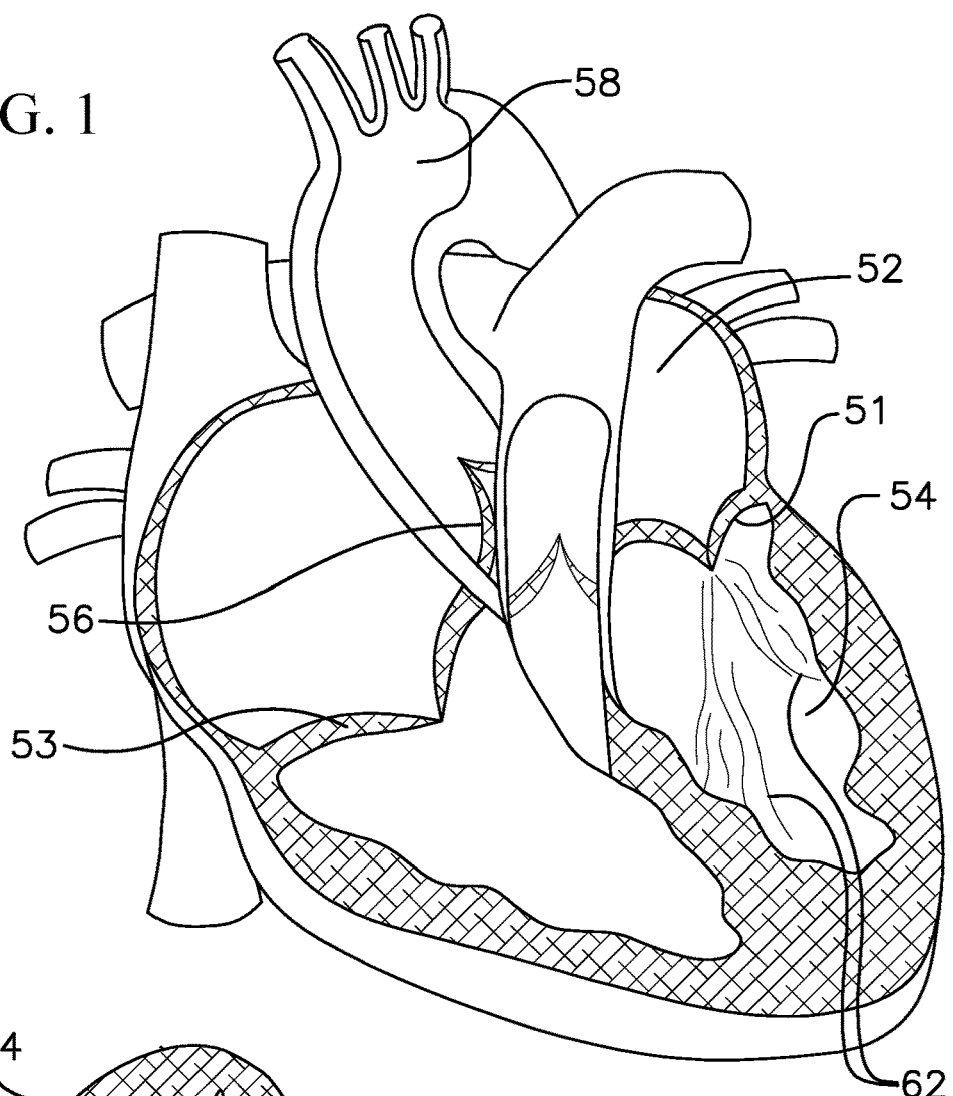
FIG. 1 shows a schematic cross-sectional view of a human heart.
Figure 2:
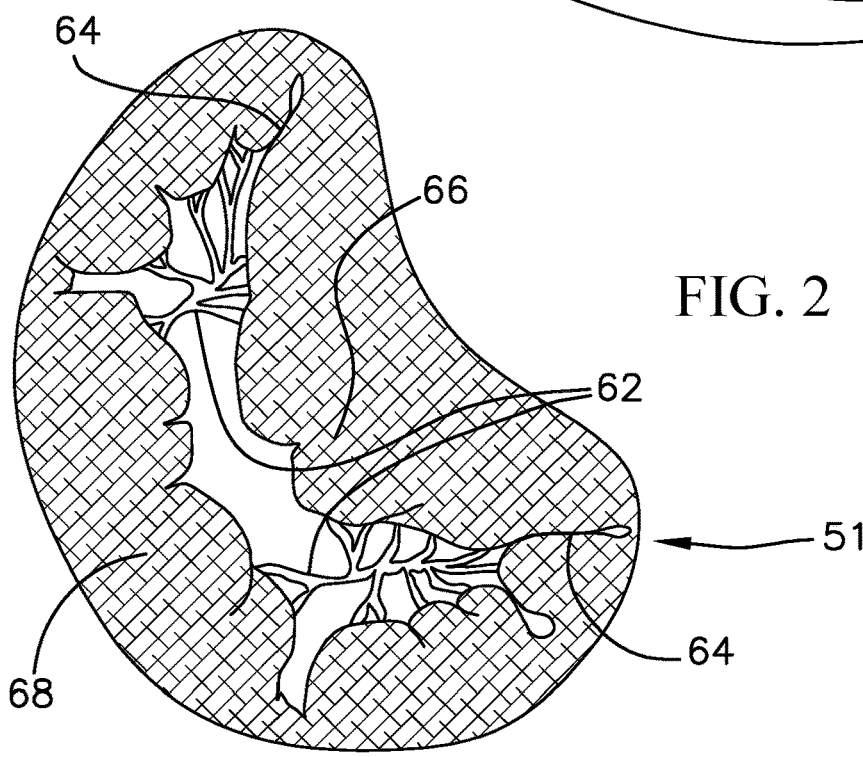
FIG. 2 shows a schematic top view of a mitral valve annulus of a heart.

The following description and accompanying figures, which describe and show certain embodiments, are made to demonstrate, in a non-limiting manner, several possible configurations of systems, devices, apparatuses, components, methods, etc. that may be used for various aspects and features of the present disclosure. As one example, various systems, devices/apparatuses, components, methods, etc. are described herein that may relate to mitral valve procedures. However, specific examples provided are not intended to be limiting, e.g., the systems, devices/apparatuses, components, methods, etc. can be adapted for use in other valves beyond the mitral valve (e.g., in the tricuspid valve).

Disclosed herein are embodiments of deployment tools that are intended to facilitate implantation of prosthetic heart valves at one of the native mitral, aortic, tricuspid, or pulmonary valve regions of a human heart, as well as methods of using the same. The prosthetic valves can be expandable transcatheter heart valves ("THVs"). The deployment tools can be used to deploy anchoring or docking devices that provide a more stable docking site to secure prosthetic valve (e.g., THVs) at the native valve region. The deployment tools include a pusher tool or mechanism that facilitates easier and more accurate delivery and positioning of the anchoring device at the implant site, so that the anchoring devices and the THVs anchored thereto can function properly after implantation.

An example of an anchor/anchoring device/docking device is shown in FIG. 3, though other configurations or variations are also possible. Anchoring or docking device 1 is a coil that is substantially helical or includes coils that are helical with a plurality of turns extending along a central axis of the docking device 1, where the coil(s) can have various differently sized and shaped sections. The docking device 1 is configured to best fit at the mitral and tricuspid positions, but can be shaped similarly or modified in other embodiments for better accommodation at other native valve positions as well. U.S. patent application Ser. No. 15/682,287 and U.S. patent application Ser. No. 15/684,836 include additional examples and details of anchors/anchoring devices/docking devices that can be used with the systems, devices, apparatuses, methods, etc. in this disclosure, and each of these applications is incorporated by reference in their entirety.

The docking device 1 includes a central region/portion 10 with approximately three full coil turns having substantially equal inner diameters. The turns of the central region 10 provide the main landing or holding region for holding the THV upon implantation, and are therefore sometimes referred to as the functional coils of the anchoring device 1, since the properties of these coils contribute most to the retention of the valve prosthesis relative to the docking device 1 and the native anatomy. A size of the coils of the central region 10 is generally selected to be slightly smaller than the outer diameter of the THV after expansion, to generate a sufficient radial forces or tension between the central region and the THV to fix them relative to one another and/or pinch native tissue (e.g., native leaflets and/or chordae) therebetween.

The docking device 1 is positionable in the native valve annulus (e.g., native mitral or tricuspid valve annulus) by rotating or cork-screwing a distal or leading tip (e.g., from the right or left atrium) through the native valve annulus (e.g., into the right or left ventricle). Since the size of the coils of the central region 10 is kept relatively small, the docking device 1 further includes a distal or lower region/portion 20 that forms a leading or encircling coil/turn (e.g., a leading ventricular coil) of the docking device 1. The lower region 20 has a diameter that is greater than the diameter of the central region 10 so that the distal tip is positioned wider relative to the central axis of the docking device 1, in order to more easily navigate the distal tip of the docking device around the features of the native anatomy, such as the chordae tendineae. When the distal tip is navigated around the desired anatomy, the remaining coils, which are smaller, can be guided around the same features, thereby encircling and corralling the anatomical features slightly inwardly. The lower region 20 can be kept relatively short to reduce flow disturbances.

The anchoring or docking device can optionally include a low-friction sleeve, e.g., a PTFE sleeve, that fits around all or a portion (e.g., the leading and/or functional turns) of the anchoring or docking device. For example, the low-friction sleeve can include a lumen in which the anchoring or docking device (or a portion thereof) fits. The low-friction sleeve can make it easier to slide and/or rotate the anchoring or docking device into position with less-friction and being less likely to cause abrasions or damage to the native tissue than the surface of the anchoring or docking device. The low-friction sleeve can be removable (e.g., by pulling proximally on the sleeve while holding a pusher and the docking device in place) after the anchoring or docking device is in position in the native valve, e.g., to expose the surface of the anchoring or docking device, which can be or include portions configured (porous, braided, large surface area, etc.) to promote tissue ingrowth.

The docking device 1 also includes an enlarged proximal or upper region 30 that makes up a stabilization coil (e.g., an atrial coil) of the docking device. The enlarged upper region 30 is sized and shaped to abut or push against the walls of native anatomy (e.g., the walls of a chamber of the heart or atrium), in order to improve the ability of the docking device 1 to stay in its desired position once it has been delivered to the implant site and prior to implantation of the THV. The docking device 1 can optionally also include a generally vertical extension 40 connecting the central region 10 and the upper region/portion 30, and serving as a vertical spacer for spacing apart and forming a vertical gap between the upper region 30 and the other portions of the docking device 1. In this manner, the amount of the docking device 1 that pushes against the native annulus can be reduced, thereby reducing stress on the native tissue. The docking device 1 can also have one or more through holes 50 at or near a free proximal end of the upper region 30. The through holes 50 can serve, for example, as an attachment site for a delivery tool such as a pusher tool, pull wire, suture, etc.

Other embodiments of docking devices can have more or less turns in each of the described regions, or some regions (e.g., the enlarged upper region 30) can be omitted altogether. In some cases, widths or thicknesses of the coil of the docking device can also be varied along the length of the docking device, based for example, on desired strengths and curvatures of certain coil regions. In some embodiments, additional layers, for example, a high friction cover layer, can also be added to the docking device to facilitate more effective delivery and/or implantation/retention. Meanwhile, while a direction of the turns of the docking device 1 are arranged for counter-clockwise advancement into the ventricle, the coils can optionally be wound in the opposite direction to facilitate clockwise advancement instead.

The docking device 1 is generally flexible, and can be made of or include, for example, a shape memory material, so that the coils of the docking device 1 can be straightened for delivery through a delivery catheter. For mitral applications, the docking device 1 can be delivered to the mitral position, for example, transatrially from the left atrium, transseptally through the atrial septum, or via one of various other known access points or procedures (e.g., transapically, etc.).

Figure 4A:
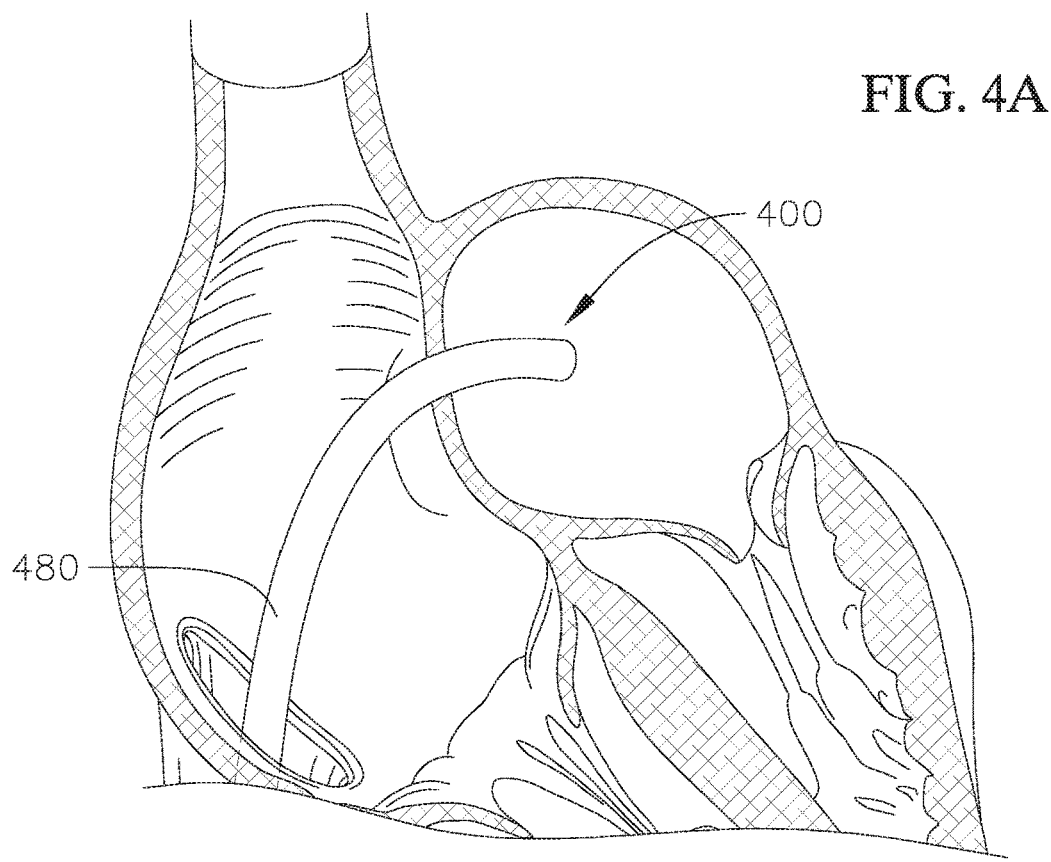
FIGS. 4A to 4D show partial perspective views of an exemplary method used for implanting an anchoring or docking device at a native valve of a heart, using a transseptal technique.
Figure 4B:
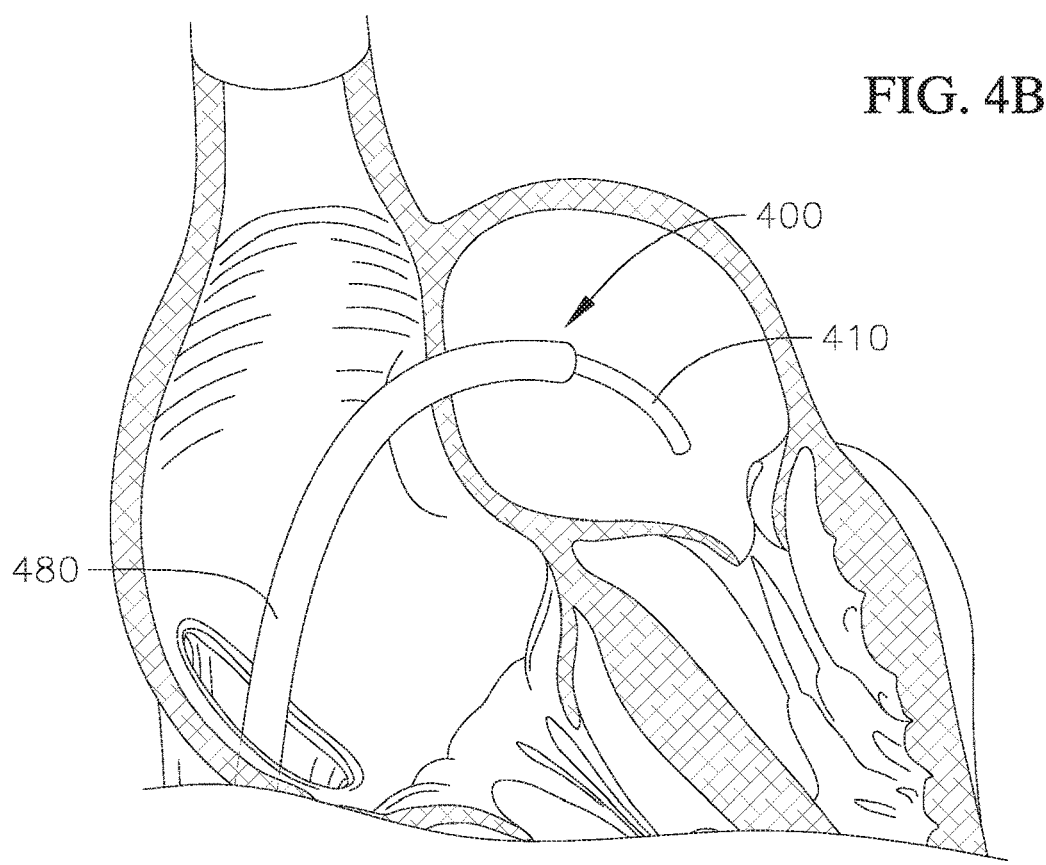

Various methods and steps can be used for delivering a docking device to a native heart valve. For example, U.S. patent application Ser. No. 15/682,287 and U.S. patent application Ser. No. 15/684,836, each incorporated by reference, describe various methods and steps that can be used. Also, FIGS. 4A to 6 show steps of an exemplary method that can be used for delivering a docking device 1 to the mitral position using a transseptal approach, where a delivery system/device 400 is advanced through the atrial septum of the heart. Referring first to FIG. 4A, the interatrial septum can be punctured, for example, at the fossa ovalis, and a larger guide sheath 480 of the delivery system/device 400, which for example, houses and protects delivery catheter 410, can first be advanced through the puncture hole and into the left atrium. In FIG. 4B, a distal region of a delivery catheter 410 is advanced out of a distal opening of the guide sheath 480 positioned in the left atrium in a substantially straight or unactuated configuration. In tricuspid procedures, it is generally unnecessary to puncture, cross, or advance through the septum.

Figure 4C:
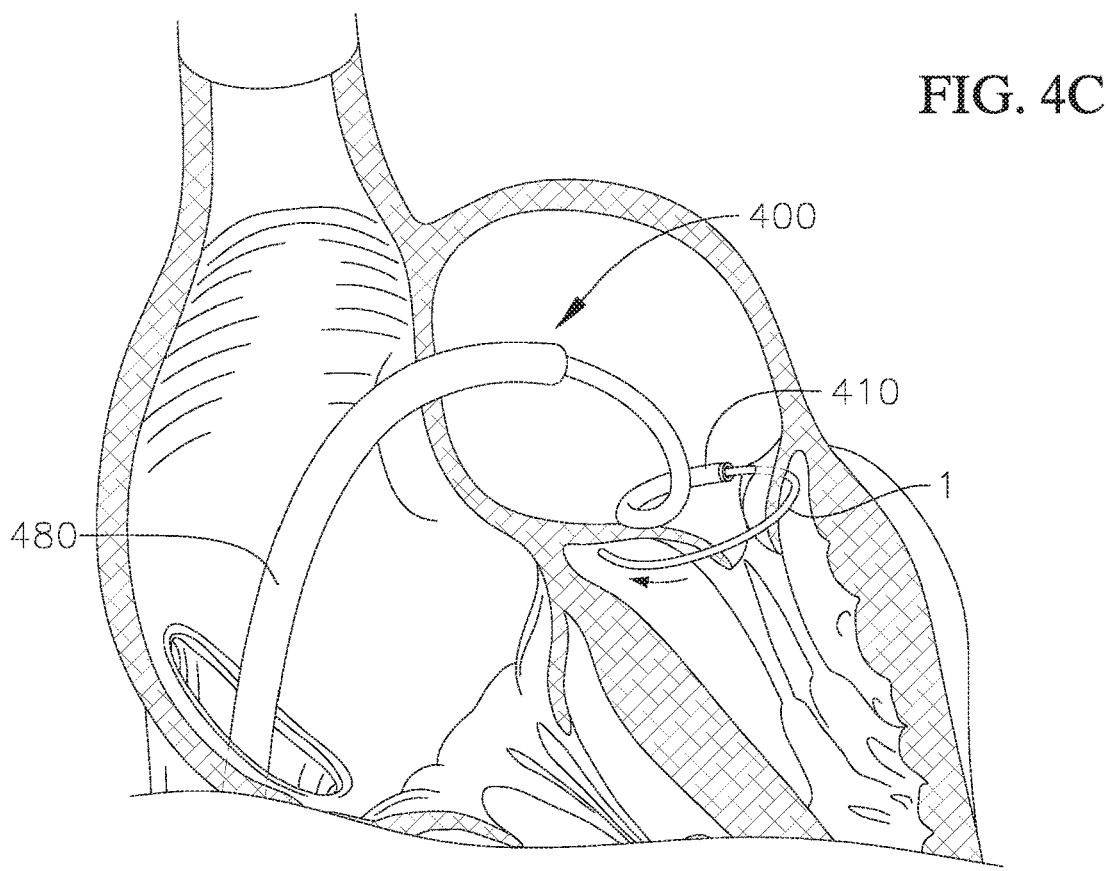

Thereafter, when in a desired region or first chamber of the heart (e.g., right or left atrium), as shown in FIG. 4C, the distal region of the delivery catheter 410 itself can be bent or otherwise actuated to prepare for delivery of the docking device 1. The distal region of the delivery catheter 410 can take various shapes based, for example, on the shape of the anchoring or docking device, the delivery site, and/or the patient's anatomy. For example, the delivery catheter 410 in FIGS. 4C and 4D delivers the docking device 1 in a clockwise direction near the A1P1 commissure.

Figure 7:
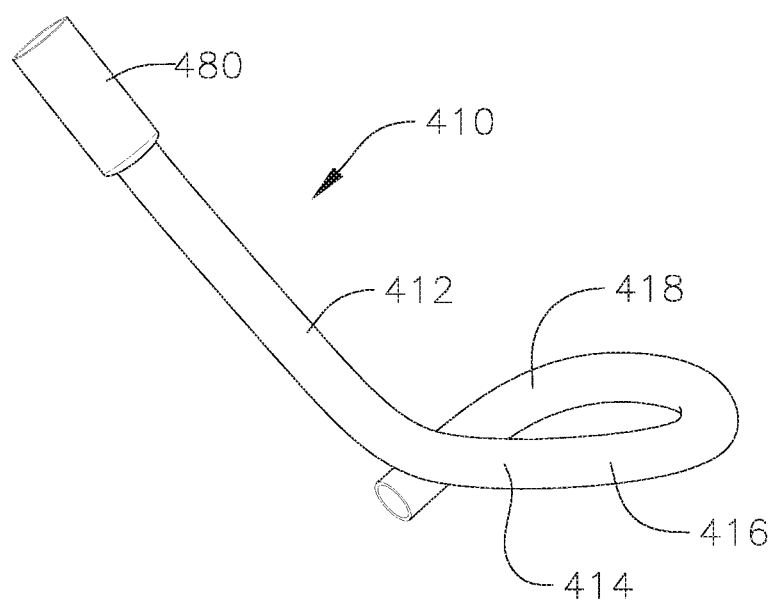
FIG. 7 shows a perspective view of a distal section of an exemplary delivery catheter useable for implanting an anchoring or docking device at a native valve.

In one embodiment, for example, as shown in FIG. 7, the distal region of the delivery catheter 410 includes a first substantially straight portion 412 extending from the guide sheath 480, followed distally by a shallow curved portion 414 to bend the distal region of the delivery catheter 410 towards the mitral plane. The shallow curved portion 414 is followed by a circular portion 416 that curves in a counter-clockwise direction (or optionally a clockwise direction) around and substantially planar to the native annulus (e.g., mitral or tricuspid annulus) to provide a general delivery path for the docking device 1. Distal to the circular portion 416 can further be a flexible end portion 418 that can be angled or pointed slightly downwards. The flexible end portion 418 can be used to point the distal opening of the delivery catheter 410 downwards towards and/or into a commissure, for example, commissure A3P3 of the mitral valve, to facilitate easier advancement of the docking device 1 into another or second chamber of the heart (e.g., the left ventricle or right ventricle). The distal opening can be positioned adjacent the commissure and the anchoring or docking device pushed out of the opening and through the commissure, or the distal opening can be positioned at or just past the commissure such that the anchoring or docking device is pushed out of the opening directly into the second chamber.

The delivery catheter 410 can include multiple control or pull wires (e.g., 2-6 pull wires) arranged and configured such that applying tension to the control/pull wires causes the distal region of the delivery catheter 410 to curve and/or shape as desired. In one embodiment, at least two control/pull wires run through a wall of the delivery catheter and terminate at different locations in the distal region such that each control/pull wire causes a different portion of the distal region to curve when tensioned or pulled. The wires can be pulled directly or have controls (e.g., handles, tabs, knobs, buttons, inputs, and/or other components) for imparting tension and/or relaxing tension of the control wires/pull wires.

Referring again to FIG. 4C, after the distal region of the delivery catheter 410 has been actuated to a delivery position, a first stage of coil delivery can be performed, where the docking device 1 is extruded or pushed out from a distal opening of the delivery catheter 410, through the native valve (e.g., mitral or tricuspid valve, such as through a commissure of the valve), and into the second chamber or left ventricle. The distal end of the docking device 1 can then be rotated around to encircle at least some of the anatomy in the second chamber or ventricle (e.g., leaflets and/or chordae) to corral the anatomy within the coils of the docking device 1. This advancement of the docking device 1 through and/or out of the delivery catheter 410 can be accomplished, for example, with a pusher tool 430 according to embodiments of the invention, as will be described in more detail below. During delivery, the docking device 1 can be held in the delivery catheter 410 in a straightened or relatively straight configuration for easier maneuverability through the delivery catheter 410. Thereafter, as the docking device 1 exits the delivery catheter 410, the docking device 1 can return to its original or shape-memory coiled or curved shape.

Figure 4D:
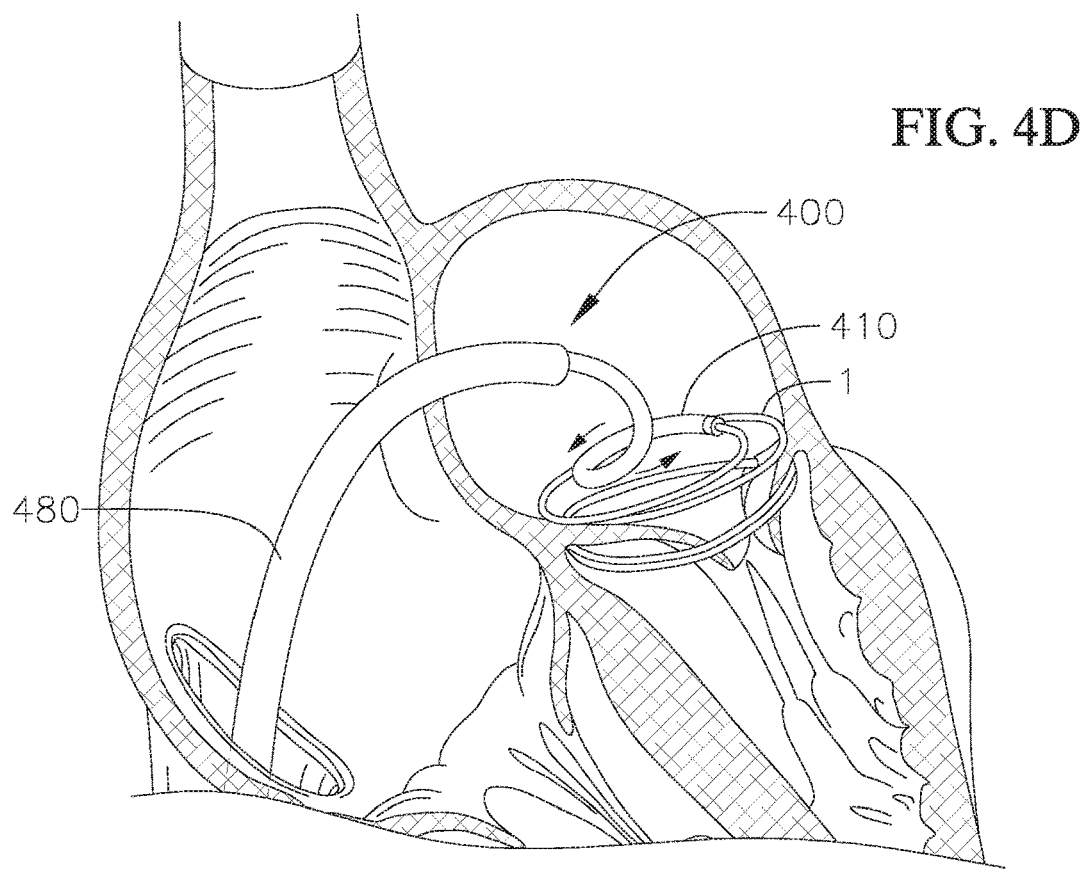

After a desired amount of the docking device 1 has been advanced into the second chamber of the heart (e.g., left or right ventricle), the rest of the docking device 1 can then be deployed or released into the first chamber of the heart (e.g., left or right atrium) during a second stage of coil delivery. FIG. 4D shows one method of releasing the upper portion or stabilization coil/turn (e.g., atrial portion) of the docking device 1 into the first chamber (e.g., left or right atrium). In FIG. 4D, the distal region of the delivery catheter 410 is pulled and/or rotated backwards, while the docking device 1 is held at substantially the same position and orientation, until the entire docking device 1 is released from the delivery catheter 410. For example, when the docking device 1 is advanced clockwise out of the delivery catheter 410 as shown in FIG. 4C, the delivery catheter can thereafter be pulled (and/or rotated counter-clockwise), as shown in FIG. 4D, to release the upper portion or stabilization coil/turn (e.g., atrial portion) of the docking device 1 therefrom. The pusher tool 430 can be adjusted during this procedure to extrude and/or push out the anchoring or docking device 1 from the delivery catheter 410 and/or pull/retract the delivery catheter while a position of the docking device 1 relative to the native anatomy (e.g., mitral or tricuspid anatomy) is maintained. In this manner, a lower portion (e.g., ventricular position) of the docking device 1 does not have to be adjusted or readjusted during or after delivery of the upper portion (e.g., atrial portion) of the docking device 1. Various other methods of releasing the upper portion of the docking device 1 can also be employed in other embodiments.

Figure 5:
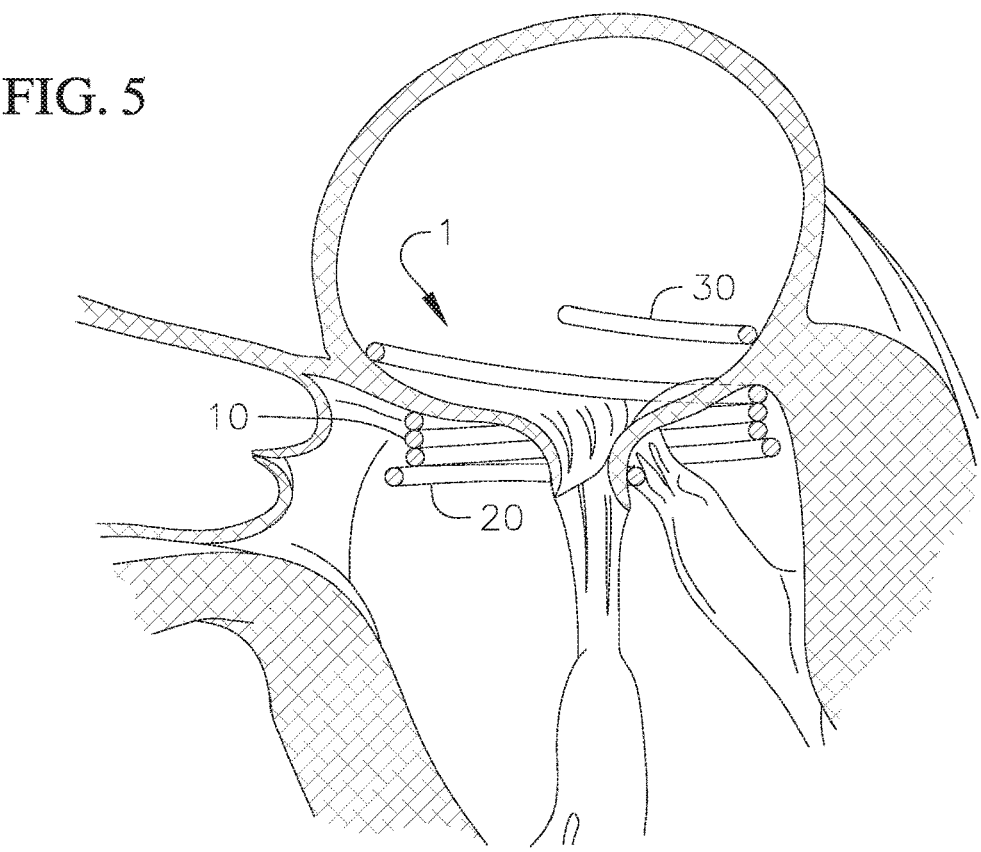
FIG. 5 shows a cross-sectional view of an exemplary anchoring or docking device positioned at the native valve of the heart prior to delivery of a prosthetic heart valve.

After the docking device 1 is fully deployed and adjusted to a desired position at the implant site, any connections between the pusher tool 430 and the docking device 1 (e.g., connection sutures) can be detached, and the delivery device 400 can be removed from the implant site. FIG. 5 shows a cross-sectional view of a portion of a patient's heart with the docking device 1 implanted at the mitral position and prior to delivery of the THV. The enlarged upper portion/region or stabilization turn/coil 30 of the docking device 1 pushes against the first chamber walls (e.g., atrial walls) to help temporarily hold the docking device 1 at a desired position. The THV is then advanced through and expanded in the docking device 1. The THV can be advanced using the same or a different delivery catheter.

Figure 6:
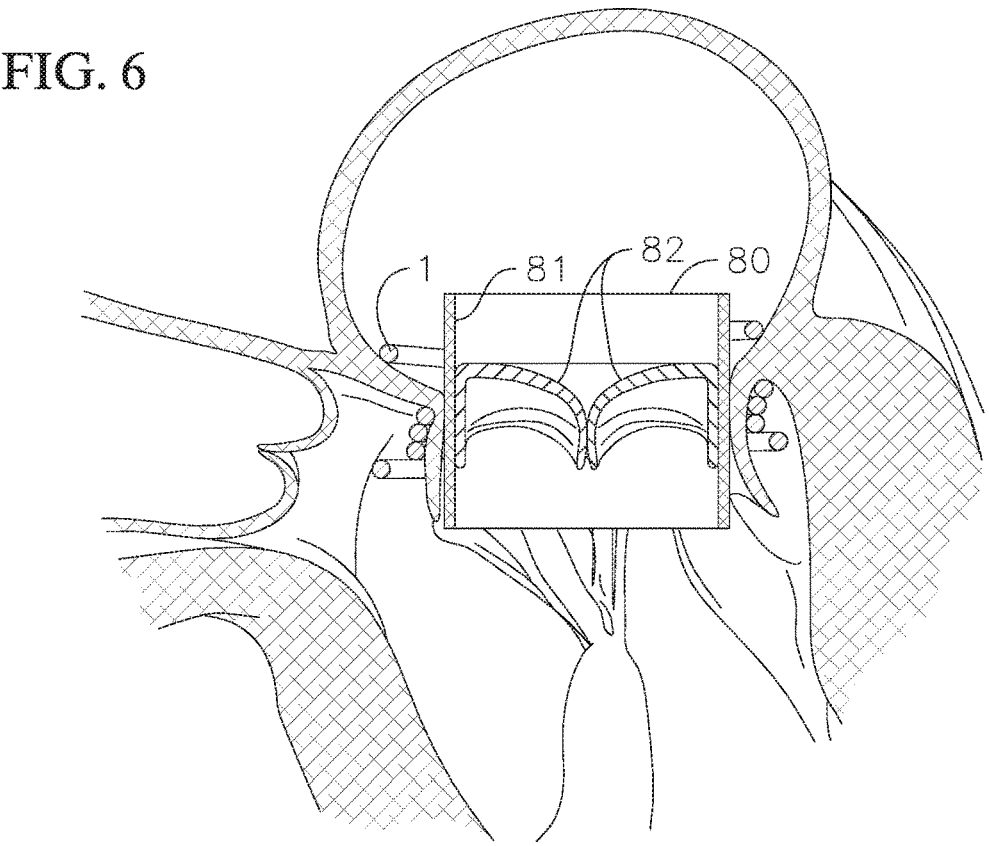
FIG. 6 shows a cross-sectional view of the anchoring or docking device and a prosthetic heart valve finally implanted at the native valve of the heart.

FIG. 6 shows a cross-sectional view of a portion of the heart with both the docking device 1 and a THV 80 finally implanted at the mitral position. Similar positioning can be accomplished in the tricuspid valve. Generally, the THV 80 will have an expandable frame structure 81 that houses a plurality of valve leaflets 82 (e.g., artificial and/or pericardial leaflets). The expandable frame structure 81 can, for example, be self-expanding, mechanically expandable, or balloon expandable. Upon expansion, radial pressures between the THV 80 and the docking device 1, as well as with the surrounding anatomy, securely hold the entire assembly in place at the native valve position (e.g., mitral or tricuspid position).

Figure 8:
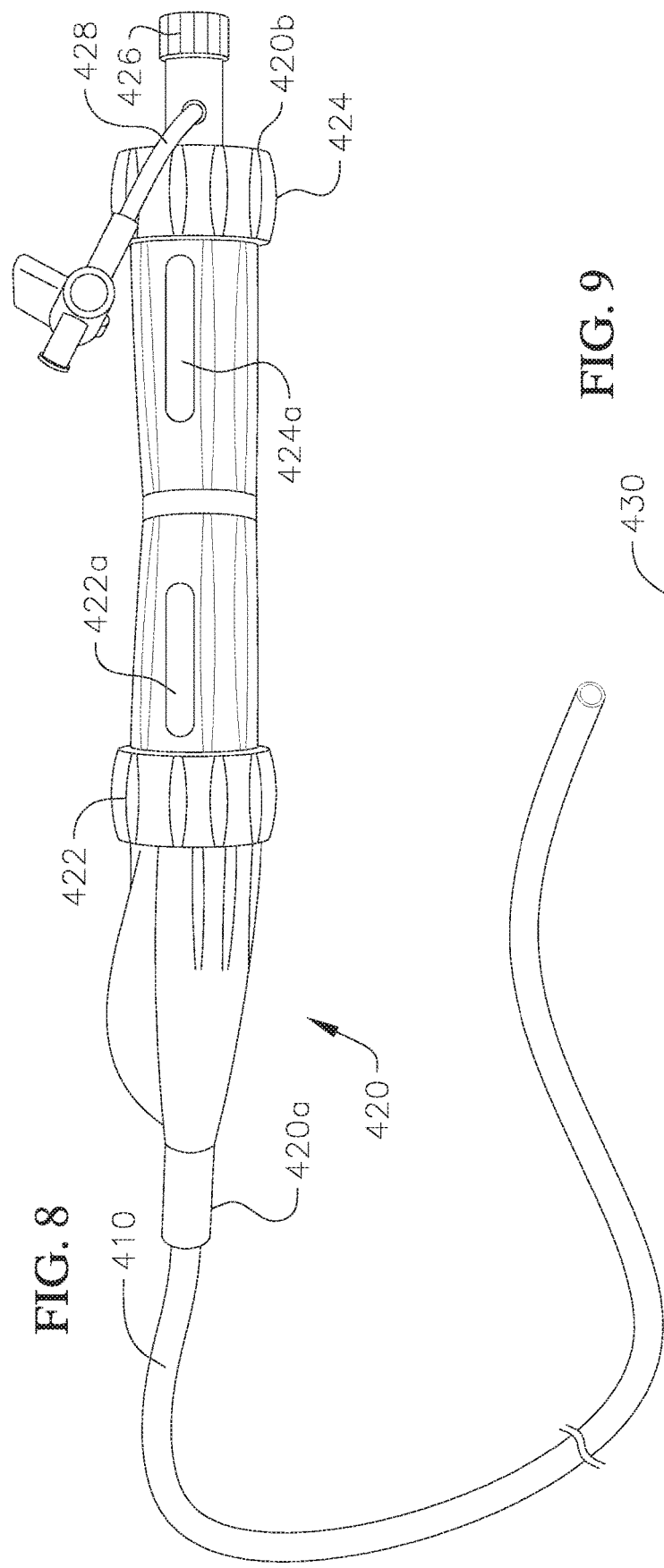
FIG. 8 shows a perspective view of an exemplary catheter handle of a delivery catheter that can be used to control the delivery catheter or portions thereof.

As discussed above, FIG. 7 shows a perspective view of a distal section of the delivery catheter 410 in an exemplary actuated delivery state, but other actuated delivery states are possible. Control or actuation of the distal section of the delivery catheter 410 can be accomplished, for example, through various controls that are integrated into a handle that is connected to a proximal end of the delivery catheter 410. FIG. 8 shows a perspective view of an embodiment of a catheter handle 420 connected to the delivery catheter 410. The catheter handle 420 includes an elongated main body that is connected to the delivery catheter 410 at its distal end 420a. The main body of the catheter handle 420 provides a central lumen or tubular bore extending therethrough (not shown) that is connected to the delivery catheter 410, to provide access to the delivery catheter 410 from a proximal end 420b of the catheter handle 420.

The catheter handle 420 can further include two controls 422, 424 configured to adjust the shape or otherwise actuate the distal region of the delivery catheter 410, for example, to the configuration shown in FIG. 7 or another configuration with two regions/portions curved in different dimensions. A first control 422 can be arranged in the form of a knob that can rotate around the catheter handle 420 (e.g., coaxial with the handle), and can control, for example, an internal threaded member (not shown) that increases or decreases the tension in a first control wire or pull wire connected to a first region (e.g., a first distal region) of the delivery catheter 410. The first control knob 422 (or optionally the second control knob 424)) can be used to adjust the shallow curved portion 414 for aligning the first region of the delivery catheter 410 with the plane of the native valve annulus for example, the mitral plane. Meanwhile, a second control 424 can also be arranged in the form of a knob that can also rotate around the catheter handle 420 (e.g., coaxial with the handle). The second control knob 424 can control another internal threaded member (not shown) that increases or decreases the tension in a second control wire or pull wire that is connected to a second region (e.g., a second distal region or a region distal to or distally adjacent to the first region) of the delivery catheter 410, for example, to bend the circular portion 416 around the native valve annulus. In this manner, the handle can independently control the degree of flexion or actuation in multiple dimensions (e.g., in each of the shallow curved portions 414 and the circular portion 416), for more precise positioning and delivery of the docking device 1. Additional control wires or pull wires are also possible as discussed previously, and these can be similar to those discussed here and can be controlled with additional controls or knobs similar to controls 422, 424 or with the same controls.

The handle can, optionally, also include one or more indicators, such as indicators 422a, 424a, that respectively identify an amount of flexion or actuation of the delivery catheter 410 effected by each of the controls (e.g., by controls 422, 424). The indicators 422a, 424a, can each be, for example, a window that is integrated into the catheter handle 420, with a level indicator and a key which identifies how much each control is actuating the delivery catheter 410. In some embodiments, a position of an internal feature associated with the controls 422, 424, for example, the internal threaded members which translate axially relative to the catheter handle 420 when one of the controls 422, 424 is turned, can also serve as a level indicator through the indicators 422a, 424a. In this manner, the delivery catheter 410 can be more precisely controlled or adjusted. In some embodiments, a third controller is also included to control the distal end portion 418, or the control of the distal end portion 418 can be integrated into one of the existing controllers, for example, the second control 424.

The catheter handle 420 can also include additional features. For example, in FIG. 8, the catheter handle 420 includes a collet mechanism 426 that can lock, for example, a position of a pusher body, a pusher wire, or other component relative to the catheter handle 420. In FIG. 8, the proximal end 420b of the handle further includes a proximal seal and flushing port 428 to facilitate easy flushing of the handle, delivery catheter 410, and/or other components of the delivery device 400. In other embodiments, a handle for controlling the delivery catheter 410 can include any of various other features which can assist in facilitating more precise and/or better handling of the delivery catheter 410.

While the above features of the catheter handle 420 facilitate the control of the distal region of the delivery catheter 410 in preparation for delivering the docking device 1, another tool or mechanism can be used to physically advance and retract the docking device 1 through the delivery catheter 410 and/or maintain its position.

Figure 9:
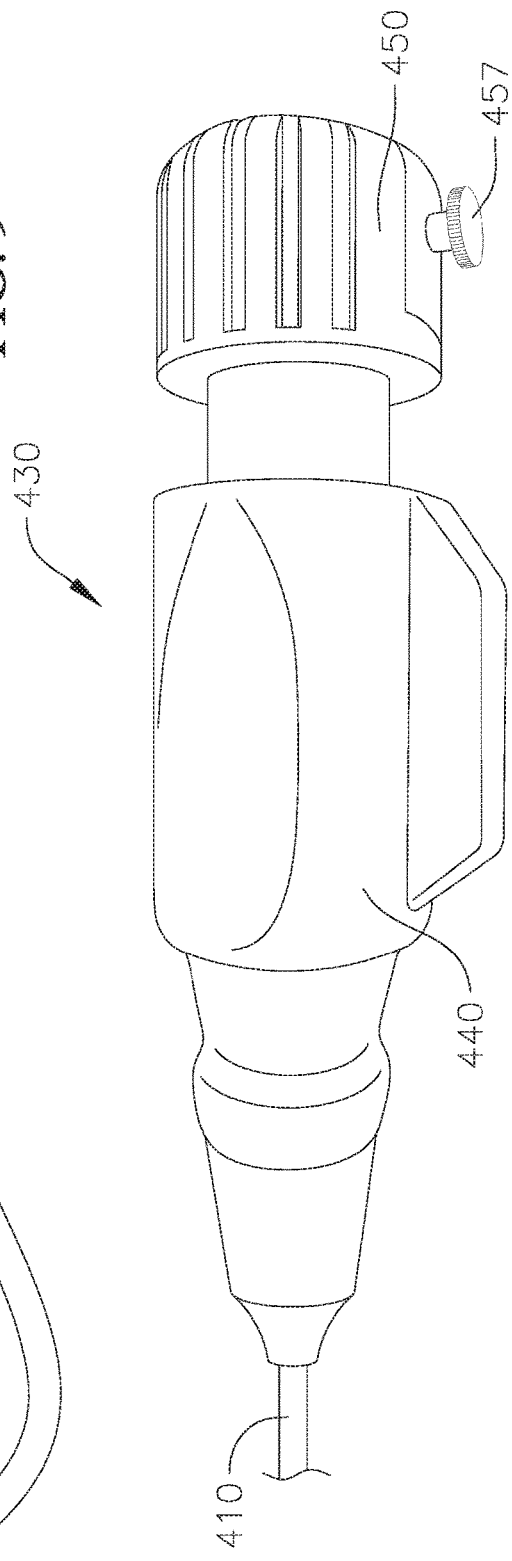
FIG. 9 shows a perspective view of an exemplary pusher tool, where the pusher tool is useable to advance the anchoring or docking device through and/or out of a delivery catheter.
Figure 10:
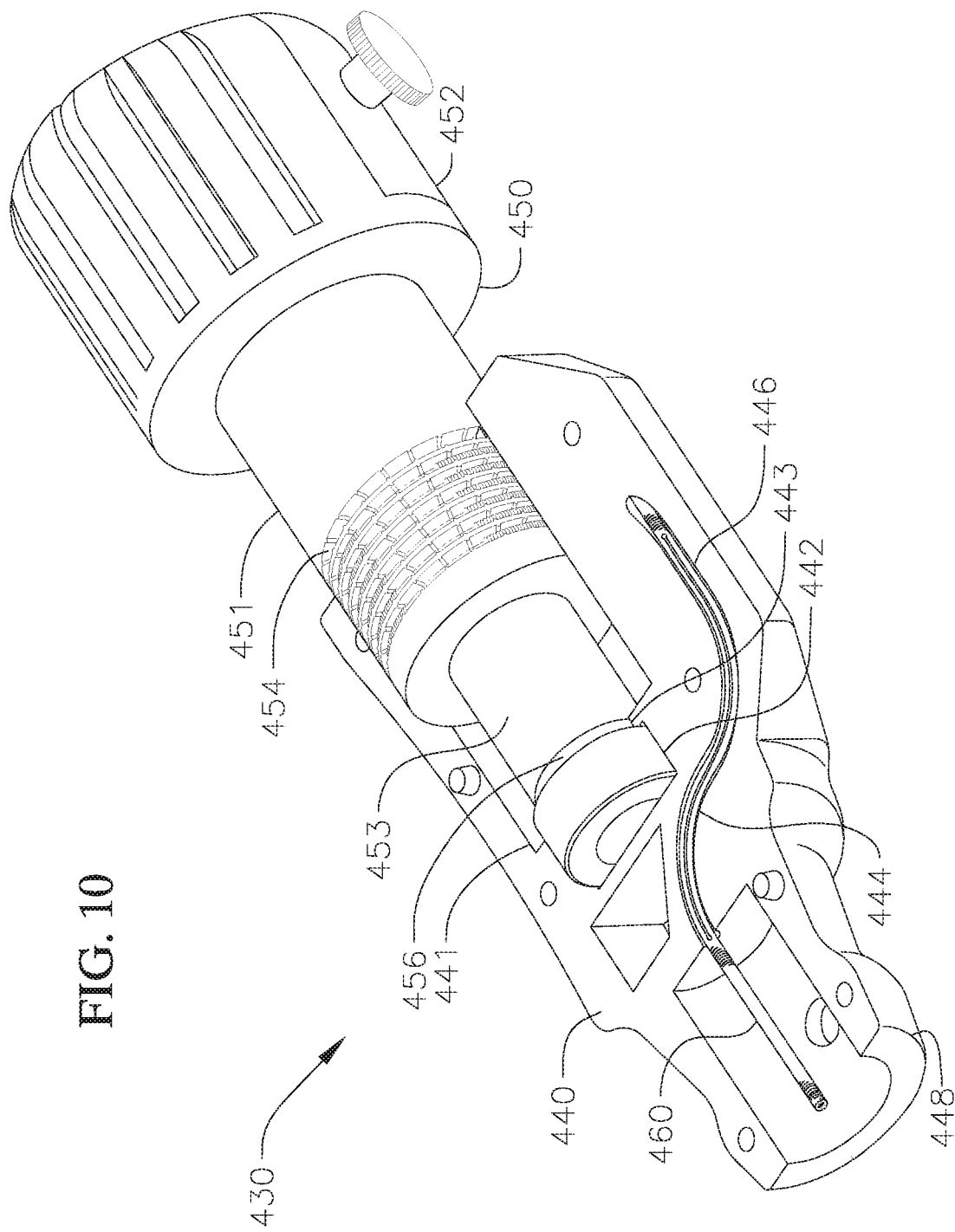
FIG. 10 shows a perspective and partial cross-sectional view of the pusher tool of FIG. 9.

FIG. 9 shows a perspective view of an exemplary pusher tool 430, and FIG. 10 shows a perspective and partial cross-sectional view of the pusher tool 430 of FIG. 9. The pusher tool 430 in FIGS. 9 and 10 is presented schematically, and it is to be understood that a pusher tool 430 can either be an entirely separate tool from the catheter handle described above with respect to FIG. 8, or in some embodiments, can be integrally formed with or combined with other embodiments of catheter handles. For example, in some embodiments, the catheter handle 420 in FIG. 8 can be designed to have an integrated pusher mechanism with features similar to or the same as the pusher mechanism discussed below, so that a separate pusher tool is not needed.

Referring to FIGS. 9 and 10, an exemplary pusher tool 430 can include a handle body 440, a knob 450, and/or a pusher wire or tube 460. While various features/components and arrangements are described as examples, all the described features/components and arrangements are not required. For example, one embodiment can have a handle body 440 and a knob 450 that can rotate relative to each other to cause translational or axial movement of these components relative to each other, while another embodiment may not have one or both of these features and/or these features may not be arranged for relative axial or translational movement. One embodiment can just have a knob that rotates a rotational member and a pusher wire/tube that can wrap/wind on or off the rotational member to extend or retract in the delivery catheter. The pusher tool could also have a body with a fixed relationship to the pusher wire/tube that does not involve rotation or winding. The pusher tool can be connectable or not connectable to the delivery catheter.

As shown in the illustrated example in FIG. 10, the handle body 440 can have an elongated and generally cylindrical profile. A central bore 441 can extend from a proximal end of the handle body 440 towards a distal end of the handle body 440. The central bore 441 can define a generally cylindrical space within the handle body 440, into which a base 451 of the knob 450 can extend. The distal end of the central bore 441 can be closed, and can have a portion 442 that is also substantially cylindrical, with a reduced diameter compared to that of the rest of the central bore 441. In addition, between the portion 442 and the other portions of the central bore 441, an engagement feature 443, such as a projection or a groove, can be formed at an inner wall of the handle body 440. The portion 442 of the bore 441 and/or the engagement feature 443 can be utilized to help attach the handle body 440 with the knob 450.

The handle body 440 can, optionally, also define a tunnel or pathway 444 that connects the central bore 441 with the distal end of the handle body 440. The tunnel 444 can include a first region 445 that extends substantially tangentially from the cylindrical profile of the central bore 441 (see, e.g., FIG. 11), and can include a second region 446 that turns from the first region 445 towards the distal end of the handle body 440, to provide a pathway for the pusher or pusher wire 460 to run from the central bore 441 to the distal end of the handle body 440. As can also be seen in FIG. 11, in some embodiments, an inner wall of the handle body 440 can also include a guiding key 447, which can be a small projection, to guide the movement of the knob 450 relative to the handle body 440. Meanwhile, at the distal end of the handle body 440, a bore, luer, or other structural feature 448 can be provided for attaching and fixing the handle body 440 to other parts of the delivery device 400, for example, to a delivery catheter 410 or a catheter handle 420. In some embodiments, the body of the handle shell 440 is a monolithic piece, while in other embodiments, the handle body 440 can be multiple pieces, for example, two halves that can be assembled together.

Meanwhile, the knob 450 of the pusher or pusher tool 430 can include a base 451, an enlarged head region 452 at one end for easier handling and rotating by a practitioner or other end user, and a knob support 453 at an opposite end for connecting the knob 450 to the handle body 440. The base 451 of the knob 450 can be substantially cylindrical and sized for insertion into the central bore 441 of the handle body 440. A diameter of the base 451 can be slightly smaller than a diameter of the central bore 441, so that the base 451 fits snugly in, and can still turn or rotate while positioned in, the central bore 441.

Near a distal end of the base 451 of the knob 450, a slot or canal 454 can be formed in an exterior surface of the base 451 and can extend multiple times around the exterior surface of the base 451 in a spiraling or helical manner. The slot 454 can be sufficiently sized to hold the pusher or pusher wire 460 therein, so that the pusher wire 460 also wraps around the base 451 of the knob 450 in a spiraling or helical manner while held in the slot 454. In some cases, the spiraling shape the pusher wire 460 is held in is similar to a shape and size of the docking device 1 (e.g., of a portion of the docking device 1) when the docking device 1 is deployed, which can facilitate easier shaping of the pusher wire 460 through the curved distal portions of the delivery catheter 410 during delivery of the docking device 1. Furthermore, when the handle body 440 and the knob 450 are connected, the slot 454 can be positioned fully within the central bore 441 of the handle body 440. Therefore, due to a snug fit between the central bore 441 of the handle body 440 and the base 451 of the knob 450, the slot 454 can be substantially enclosed by the handle body 440 and the knob 450, so that portions of the pusher wire 460 that are held in the slot 454 are entirely supported in all radial directions around a central axis of the pusher tool 430, preventing the pusher wire 460 from spreading out of or otherwise escaping the slot 454 of the knob 450, and ensuring proper functionality of the pusher tool 430.

Figure 12:
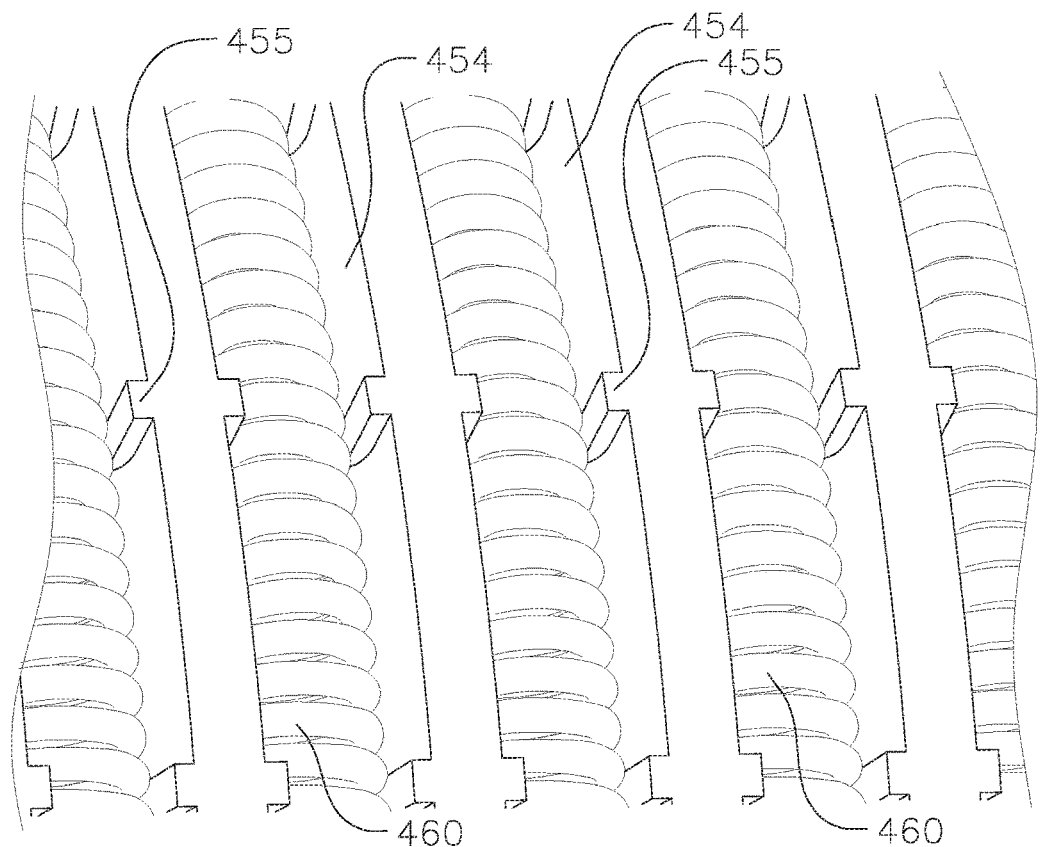
FIG. 12 shows an enlarged view of another section of the pusher tool of FIGS. 9 and 10, including portions of an exemplary pusher wire and a slot for holding the pusher wire.

Meanwhile, as can best be seen in FIG. 12, a plurality of ribs 455 can be formed in the knob 450 that extend transversely into the slot 454. In the embodiment shown, the ribs 455 are arranged in pairs that extend from opposite sides of the slot 454 towards one another, and a plurality of such pairs of ribs 455 are positioned at intervals along at least part of the length of the slot 454. In other embodiments, other rib arrangements can be formed in the slot 454, so long as the pusher wire 460 can extend through the slot 454 past each of the ribs 455. The ribs 455 increase a friction or abutting force between the pusher wire 460 and the knob 450, which results in a higher pushing ability or force that the pusher wire 460 can impart on the docking device 1, when compared for example, to a pusher tool where the only push force or abutting force is applied at a proximal end of the pusher wire by the pusher tool.

At one end of the base 451, the knob 450 can have an enlarged head region 452. The enlarged head region 452 can be adapted for easy handling and rotation by a practitioner or other end user. In the embodiment shown, the enlarged head region 452 is also cylindrical, with a diameter that is greater than a diameter of the base 451, and includes a plurality of longitudinal ribs or gripping features for improved grip. The enlarged head region 452, in other embodiments, can be designed with different shapes and sizes, so long as safe and easy handling and manipulation of the knob 450 relative to the handle body 440 can be achieved.

Referring back to FIG. 10, the knob support 453 shown is a cylindrical or tubular piece that extends away from the base 451 of the knob 450 on a side opposite the enlarged head region 452, with a diameter that is less than the diameter of the base 451. The knob support 453 can connect the knob 450 to the handle body 440. For example, the knob support 453 can be sized to fit inside the smaller distal portion 442 of the central bore 441 of the handle body 440, and can have a circumferentially extending groove 456 that is configured to engage the projecting engagement feature 443 of the handle body 440, to prevent the knob support 453, as well as the rest of the knob 450, from falling out or disconnecting from the handle body 440. In some embodiments, the locations of the groove and projection can be switched, or other engagement features can be utilized, so long as the knob 450 can freely turn relative to the handle body 440. The knob support 453 can be axially movable relative to the rest of the knob 450, so that the knob 450 can still move axially relative to the handle body 440 in order to maintain alignment of the respective pathways for the pusher wire 460. The knob support 453 can extend, for example, into a bore formed at a distal end of the base 451 of the knob 450, and an additional engagement feature (not shown) holds the knob support 453 and the rest of the knob 450 together. In one embodiment, the knob support 453 is formed monolithically with the rest of the knob 450, where the engagement between the knob support 453 and the handle body 440 can be modified to allow the knob support 453 to also move axially relative to the handle body 440.

The pusher or pusher wire 460 can connect the docking device 1 to the rest of the pusher tool 430, and can be the part or one of the parts that physically pushes or otherwise deploys, and in some embodiments, pulls or otherwise retrieves, the docking device 1 relative to the delivery catheter 410. As can be seen most clearly in FIG. 12, the exemplary pusher wire 460 in the figure is shown as being constructed as a spring wire formed by a compact and fully contracted spring. Respective diameters of the physical wire that forms the spring, as well as of the structure of the pusher wire 460 as a whole, can be selected to give the pusher wire 460 enough flexibility to wrap around and turn together with the knob 450, and with enough stiffness to push and/or resist retraction of the docking device 1 during deployment of the docking device 1, while avoiding portions of the pusher wire 460 collapsing longitudinally inside either the tunnel 444 of the handle body 440 or the slot 454 of the knob 450. In embodiments where the pusher wire 460 is constructed as a spring wire, the surface of the pusher wire 460 can also provide additional engagement features that interact with the ribs 455 in the slot 454, which can further enhance the pushing force of the pusher tool 430.

Optionally, pushers or pusher wires/tubes can be constructed in any of various different manners. For example, the pusher or pusher wire/tube can be constructed with or include a polymer tube, can be a laser cut hypotube with a polymer cover, can be a coil pipe or spring, or can be constructed with or include any other form of flexible tube, so long as axial pressures can be applied against the pusher or pusher wire/tube with minimal or no axial compression, so that the pushing of the docking device 1 is not compromised by the construction of the pusher or pusher wire 460.

Figure 13:
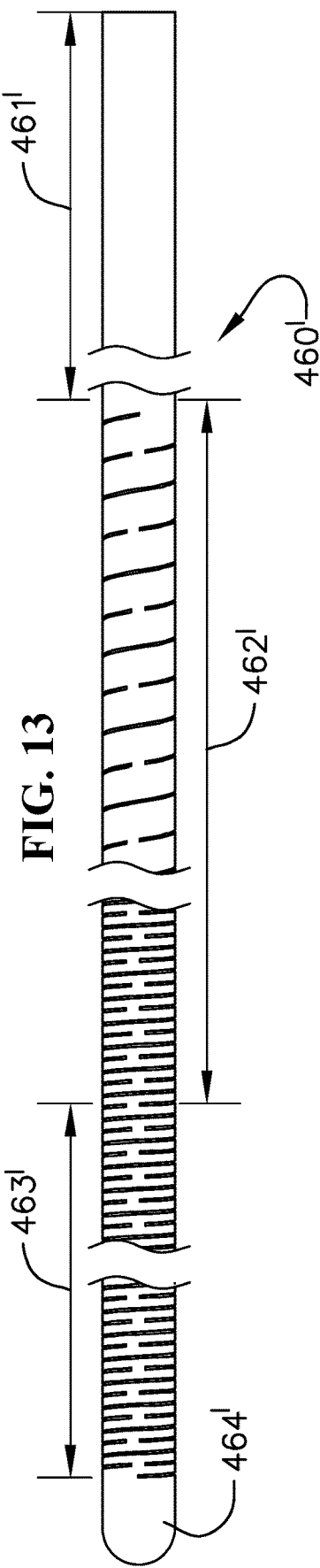
FIG. 13 shows a schematic view of an exemplary pusher tube.

In one embodiment, illustrated in FIG. 13, an exemplary pusher or pusher tube/wire 460' is constructed using a hypotube that is laser cut or otherwise cut to provide for multiple sections (e.g., three sections) with different flexibility. The pusher 460' illustrated by FIG. 13 can be used separately from the pusher tool 430 illustrated by FIGS. 9-12. A first section 461' can be formed with an uncut hypotube, so that the first section 461' forms a stiffest portion of the pusher or pusher tube 460'. A second section 462' adjacent to the first section 461' can be formed by cutting a hypotube with an interrupted cut, and the interrupted cut can, optionally, have axial intervals that decrease in a direction from the first section 461' towards a third section 463'. In this manner, the second section 462' is stiffer in a region closer to the first section 461', where the intervals between the cuts are larger, and more flexible towards the third section 463', where the intervals between the cuts are smaller. Lastly, the third section 463' can be formed by cutting the hypotube with an interrupted cut (e.g., an interrupted cut that stays constant at a small interval), so that the third section 463' is the most flexible of the three sections of the pusher or pusher tube 460'. In this or a similar manner, a pusher or pusher tube 460' can be customized so that some portions provide for stronger support, while other portions allow for more flexibility, for example, portions of the pusher 460' near the distal tip which maneuver through the distal turns of the delivery catheter 410. In other embodiments, different flexible sections can be formed in various different manners. In some embodiments, a small portion near the distal end of the pusher 460' can be left uncut, to impart extra strength to the distal tip 464' of the pusher 460'.

Figure 14:
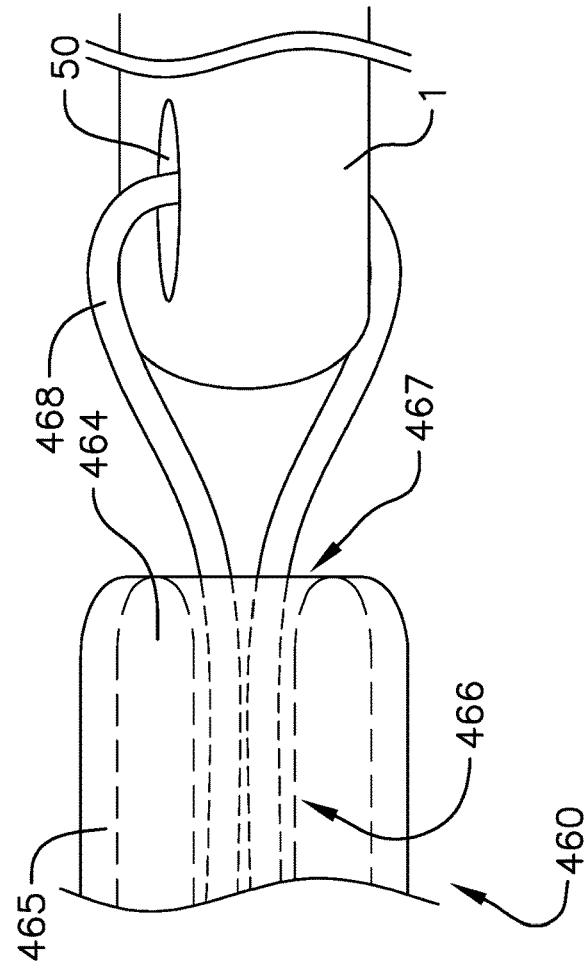
FIG. 14 shows a partial cross-sectional view of a distal tip of a pusher tube/wire that is connected to a proximal end of an anchoring or docking device.

Referring now to FIG. 14, a pusher or pusher wire/tube 460 has a distal end 464 that is constructed in an atraumatic manner. Either the pusher/pusher wire 460 discussed with respect to FIGS. 9 to 12 or the pusher/pusher tube 460' discussed with respect to FIG. 13, or any other pusher or pusher wire/tube, can employ a distal end 464 similar to or the same as that shown in FIG. 14. An atraumatic tip portion can be formed, for example, by adding an additional braided or other comparatively soft layer 465 to the distal end 464, and/or by forming a rounded or otherwise more curved tip region, to prevent damage to the docking device 1, any connecting sutures, the delivery catheter 410, and/or the patient's anatomy.

Furthermore, in some embodiments, the docking device 1 can be physically attached or connected to the distal end 464 of the pusher 460, 460', in order to maintain connection and/or enable retrieval or pulling of the docking device 1 relative to the delivery catheter 410. As shown in FIG. 14, the pusher 460 (or 460') can be formed with a central lumen 466 extending therethrough and an opening 467 at the distal tip of the pusher 460. Lumen 466 and opening 467 can provide a passageway through which a retrieval or connecting line (e.g., a retrieval or connecting suture) or other connecting feature can pass, in order to connect the pusher or pusher wire/tube to a proximal end of the docking device 1. As shown in FIG. 14, a connecting or retrieval line/suture 468 can be threaded through lumen 466, out of opening 467, and through a hole near the proximal end of the docking device 1, to connect the docking device 1 to the pusher 460. The retrieval line/suture 468 can be threaded from the distal end 464 of the pusher 460 back through the central lumen 466, and up to a proximal region of the pusher tool 430. In one embodiment, the two ends of the retrieval line/suture 468 can be anchored at or connected to a handle or other portion of the pusher tool 430, for example, to a locking knob 457 located on the enlarged head region 452 of the knob 450 (see, e.g., FIG. 9). The locking knob 457 can provide easy access to the ends of the retrieval line/suture 468, where for example, severing the retrieval or connecting line/suture 468 and/or pulling one side of the retrieval line/suture 468 until the retrieval line/suture 468 passes out of the through hole 50 on the docking device 1 disconnects the docking device 1 from the pusher or pusher wire/tube.

Figure 15:
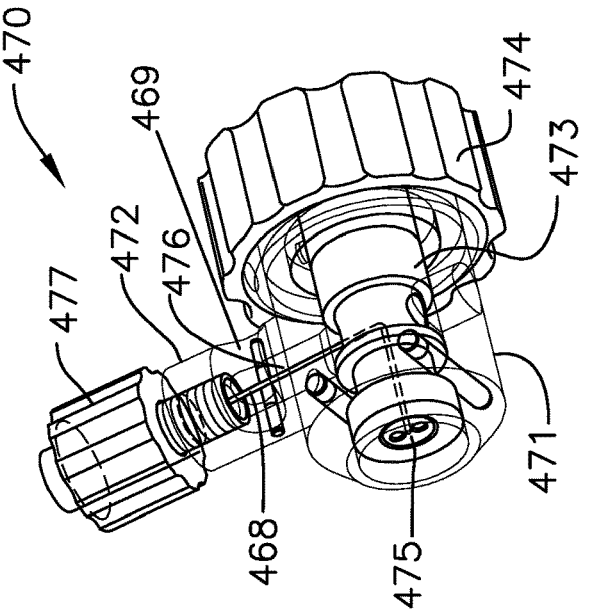
FIG. 15 shows a perspective and partial cross-sectional view of an exemplary pull wire or suture/line lock or locking mechanism for a pusher tool.

In another embodiment, shown in FIG. 15, an exemplary locking knob or exemplary suture/line lock or locking mechanism is shown. The suture locking mechanism or line locking mechanism 470 in FIG. 15 can be a component that is added to an existing assembly, for example, an assembly that does not have an integrated suture locker. In some embodiments, the suture/line lock or locking mechanism 470 itself is integrated with other portions of a pusher or pusher tool 430. The suture/line locker 470 can be used without the pusher tool 430 illustrated by FIGS. 9-12. For example, the suture locker 470 can be used with the pusher or pusher tube 460' illustrated by FIG. 13, without the pusher tool illustrated by FIGS. 9-12. The suture lock or locker 470 can include a generally T-shaped body having a first portion 471 and a second portion 472 that extends away from a central region of the first portion 471.

A rotatable member 473 can be connected through and rotatable relative to the first portion 471 of the body, and can have a handle 474 at one end that extends outside of the first portion 471 of the body. The handle 474 can facilitate turning or rotating of the rotatable member 473 relative to the first portion 471 of the body. On an end of the rotatable member 473 opposite the handle 474, an engagement feature 475 can be provided for anchoring or holding one or more ends of the connecting or retrieval line/suture 468 thereto. Meanwhile, a bore 476 can extend through the second portion 472 of the body to connect the first portion 471 of the body with a distal opening of the body. The bore 476 can create a suture route or pathway that allows the retrieval line/suture 468 to extend through the second portion 472 to the first portion 471 of the body, where the retrieval line/suture 468 can engage the rotatable member 473. Here, the retrieval line/suture 468 can be passed through or over the rotatable member 473, and can be anchored using the engagement feature 475. When the retrieval line/suture 468 is anchored to the rotatable member 473, the rotatable member 473 can act as a spool for the retrieval line/suture 468, such that rotating the handle 474 adjusts an amount of the retrieval line/suture 468 that is wound around the rotatable member 473, for increasing or decreasing a workable length and/or tension of the retrieval line/suture 468. A slot/window/cut-out 469 can be formed in the suture/line locking mechanism 470 (e.g., in the second portion 472), and the retrieval/connecting line/suture 468 can form a loop with one end or portion of the suture or loop extending over, across, and/or through the slot/window/cut-out 469, such that the portion is exposed in the slot/window/cut-out 469 and can be cut by running a knife/scalpel along the slot/window/cut-out. Cutting the line/suture in this manner can break the loop and/or release the line/suture such that it can be withdrawn and pulled out from the docking device 1, thereby releasing the docking device 1.

Latching and/or other locks/locking mechanisms can also be incorporated into the suture/line locking mechanism 470 for maintaining a position or tension of the retrieval line/suture 468. In some embodiments, the suture/line lock or locking mechanism 470 further includes a seal cap 477 for connecting the suture/line lock or locking mechanism 470 to other components of the delivery device 400, and for example, for maintaining homeostasis through the delivery device 400 when the delivery device 400 is in use.

Referring back to FIGS. 10 and 11, when the respective parts of the pusher tool 430 are assembled together, complementary features between the various components also help facilitate a smoother and more robust operation of the pusher tool 430. For example, a first region 445 of the tunnel 444 in the handle body 440 is positioned to be aligned with the slot 454 of the knob 450, and to extend at a tangent to the spiraling wrapping direction of the slot 454. In this manner, the pusher or pusher wire/tube 460 can extend, advance, and retract seamlessly between the slot 454 on the knob 450 and the first region 445 of the tunnel 444 in the handle body 440, without any turns or direction changes between the components.

Additionally, guiding key 447 on handle body 440 can also be positioned along the spiraling wrapping direction of the slot 454, for example, slightly distally to the opening into the first region 445 of the tunnel 444. The guiding key 447 can be configured, sized and shaped to allow the guiding key 447 to extend into the slot 454, and allow the slot 454 to slide over the guiding key 447. When the guiding key 447 is positioned slightly distally to the first region 445 of the tunnel 444 into which the pusher wire 460 extends, portions of the slot 454 that reach the guiding key 447 are empty and do not hold the pusher or pusher wire/tube 460. In this manner, the guiding key 447 can act as a track or guide for the axial positioning of the knob 450 relative to the handle body 440, and prevent excess axial shifting therebetween. In this manner, the guiding key 447 can always ensure that the slot 454 is concentered and axially aligned with the tangential first region 445 of the tunnel 444 when the knob 450 is turned. The design of the pusher tool 430 also facilitates storing of a relatively long pusher or pusher wire/tube 460 in a relatively compact space in handle body 440. For example, in one embodiment, a handle with a length of only about 20 cm can house and deploy a pusher or pusher wire/tube 460 with a functional length or travel length of up to 80 cm.

Operation of the pusher tool in an exemplary method will now be described in connection with delivery of a docking device to a native mitral valve, with reference to FIGS. 16A to 17B. The pusher tool 430 shown is intended to be used together with a catheter handle, for example, catheter handle 420, which can be locked together with at least the handle body 440 of the pusher tool 430. In some embodiments, the handle body 440 of the pusher tool 430 is integrally formed with the catheter handle 420. However, in each embodiment, the handle body 440 of the pusher tool 430 and catheter handle 420 can be coupled together, so that the catheter handle 420, the delivery catheter 410, and the handle body 440 of the pusher tool 430 are rotated concurrently. Therefore, when the knob 450 of the pusher 430 is held stationary, rotation of the catheter handle 420 will cause the distal region of the delivery catheter 410 to rotate, while simultaneously also rotating the handle body 440 of the pusher tool 430 relative to the knob 450, resulting in either advancing or retracting of the pusher or pusher wire/tube 460 relative to the delivery catheter 410 depending on the direction of rotation. This arrangement provides for full control of the docking device 1 relative to the delivery catheter 410 during both deployment and retrieval of the docking device 1.

Figure 16A:
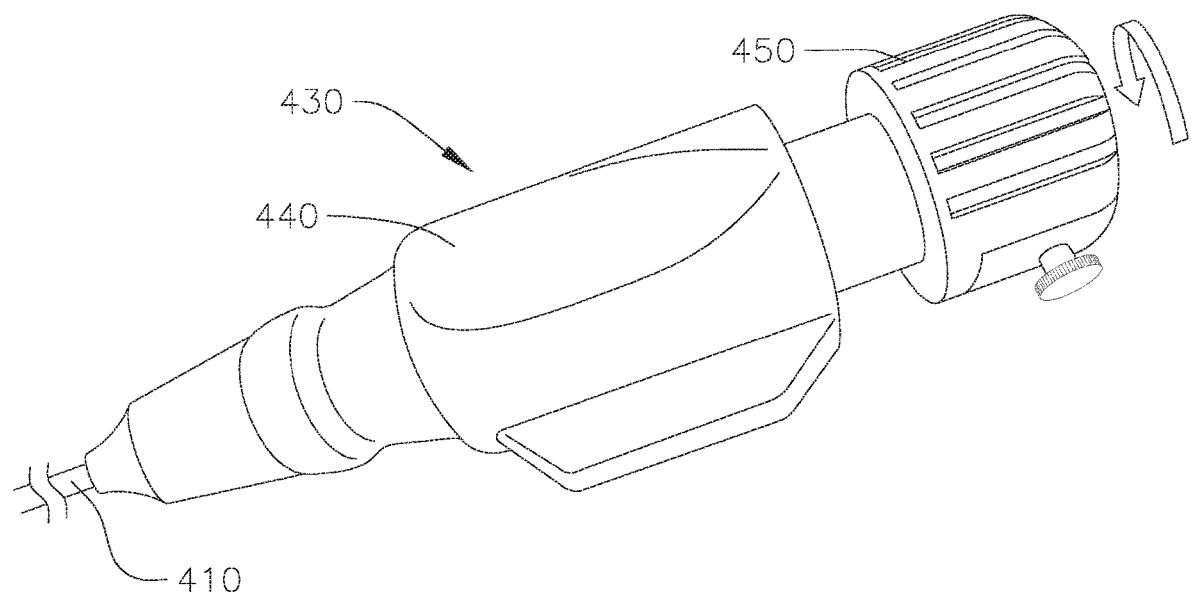
FIGS. 16A and 16B show a first step of an exemplary method of delivering an anchoring or docking device using an exemplary pusher tool.
Figure 16B:
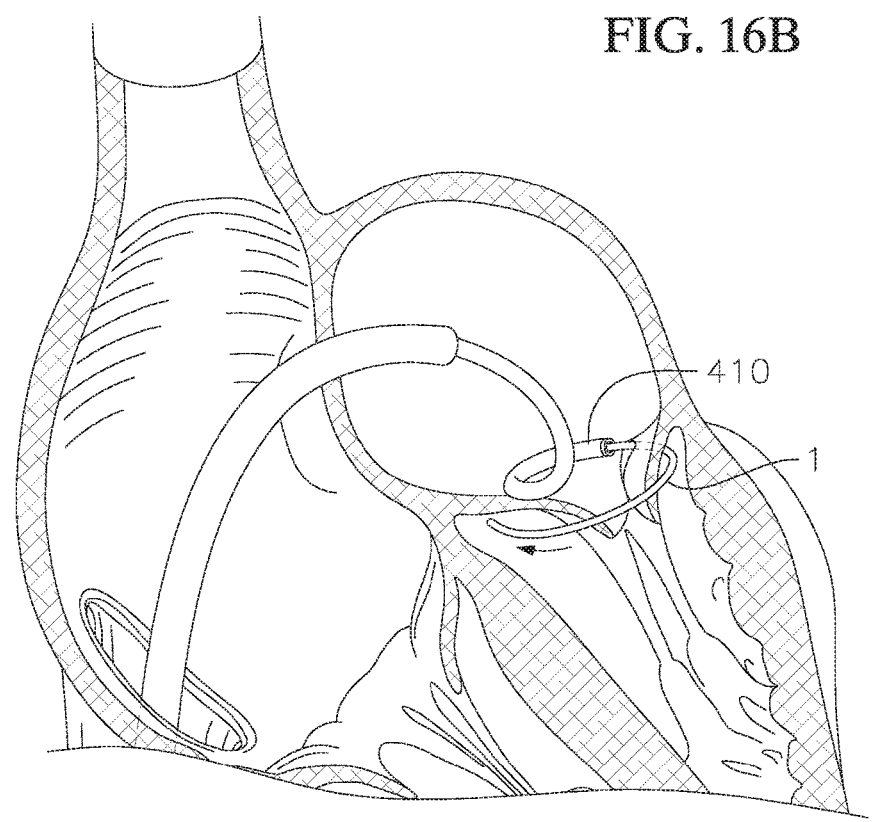

Referring now to FIGS. 16A and 16B, after the distal region of the delivery catheter 410 has been actuated or adjusted to an appropriate delivery configuration, the handle body 440 of the pusher tool 430 (and the catheter handle 420 if one is present) can be held stationary or fixed while the knob 450 is rotated, for example, in a clockwise direction relative to the other portions of the delivery device 400. Rotation of the knob 450 can unwrap the pusher or pusher wire/tube 460 from the slot 454 of the knob 450 (see, e.g., FIG. 10) and advance the pusher or pusher wire/tube 460 through the dedicated passageway formed by the tunnel 444 and out of the distal end of the handle body 440. This shifts the pusher or pusher wire/tube 460 distally relative to the delivery catheter 410, and consequently pushes the distal end of the pusher or pusher wire/tube 460 against the proximal end of the docking device 1 to advance the docking device 1 distally out of the distal opening of the delivery catheter 410. As described above, the docking device 1 can be released from or pushed out of the delivery catheter 410 at an orientation that is substantially coincident with, or angled slightly downward relative to, the plane of the native valve annulus, and is then advanced through the native valve. For example, in the mitral valve, the docking device 1 is advanced through a commissure of the valve, and into the left ventricle. Optionally, all or only a first portion of the anchoring/docking device is advanced and/or deployed at the native valve or native annulus in this way.

The various anchoring/docking devices, delivery catheters, and/or guide sheaths described in various locations in this disclosure can include one or more radiopaque markers to aid in delivery and proper positioning of the anchoring/docking device, delivery catheter, and/or guide sheath. For example, viewing the relative movement and location of a radiopaque marker on the anchoring/docking device and a radiopaque marker on the delivery catheter can indicate when a predetermined or first portion (e.g., the encircling turn/coil and/or some or all of the functional turns/coils) of the anchoring/docking device has been pushed out of the delivery catheter and into the native annulus. In one example, an operator can rotate the knob and/or advance the pusher wire/tube such that the pusher wire/tube advances the anchoring/docking device until the predetermined or first portion of the anchoring/docking device has been deployed into the native annulus by watching the relative movement of the radiopaque marker on the anchoring/docking device and the radiopaque marker on the delivery catheter (e.g., watching for when they are aligned, which can indicate the first portion has been properly deployed from the delivery catheter).

Once a desired amount or the predetermined or first portion of the anchoring/docking device (which can be determined with the use of one or more radiopaque markers on the docking device and/or delivery catheter as discussed above) of the docking device 1 has been advanced into the chamber of the heart or ventricle (e.g., left ventricle or right ventricle) and the predetermined or first portion (e.g., the ventricular coils or encircling and/or functional coils) of the docking device 1 have been positioned satisfactorily or at the native annulus, a second portion (e.g., a stabilization coil/turn or atrial coil/turn) of the anchoring device can be delivered or deployed from the delivery catheter. This can be done in a variety of ways.

For example, the knob 450 and/or pusher tool can be held stationary or fixed, so that the pusher or pusher wire/tube 460 is held at a fixed position. In this manner, the ventricular coils of the docking device 1, which is connected to or secured relative to the pusher wire/tube 460, can also be held in place without losing a desired position. The pusher tool, pusher, and/or pusher wire/tube can be locked or fixed in position (e.g., by locking or fixing a proximal end thereof, such as in a stabilizer, and/or by locking/holding/maintaining the knob in position), while the delivery catheter is pulled or retracted proximally. This can hold the anchoring device in position (e.g., because the anchoring/docking device abuts the stationary pusher or pusher wire/tube) while the delivery catheter is retracted thereby unsheathing the second portion of the anchoring/docking device from the delivery catheter. If a guide sheath is used, the guide sheath can also be locked/fixed in position (e.g., in the stabilizer) while the delivery catheter is retracted. The pusher tool, delivery catheter, and/or guide sheath can be configured and/or arranged to be separately movable with respect to each other and separately securable in a stabilizer or other locking/stabilization mechanism.

Figure 17A:
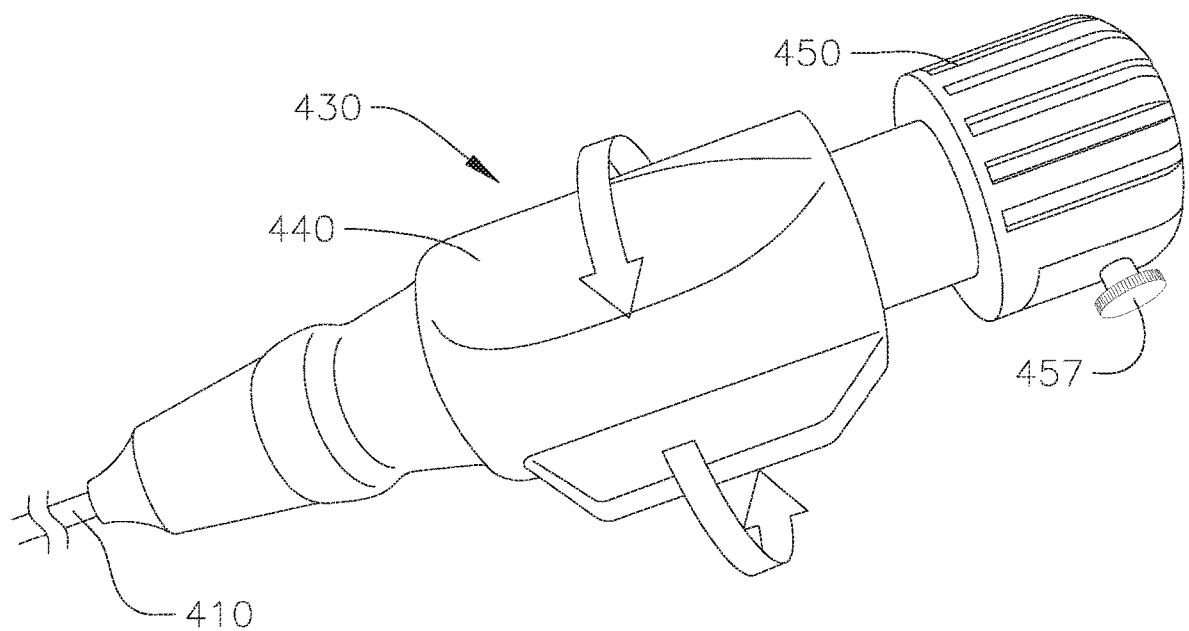
FIGS. 17A and 17B show a second step of the exemplary method of delivering the anchoring or docking device using the pusher tool.
Figure 17B:
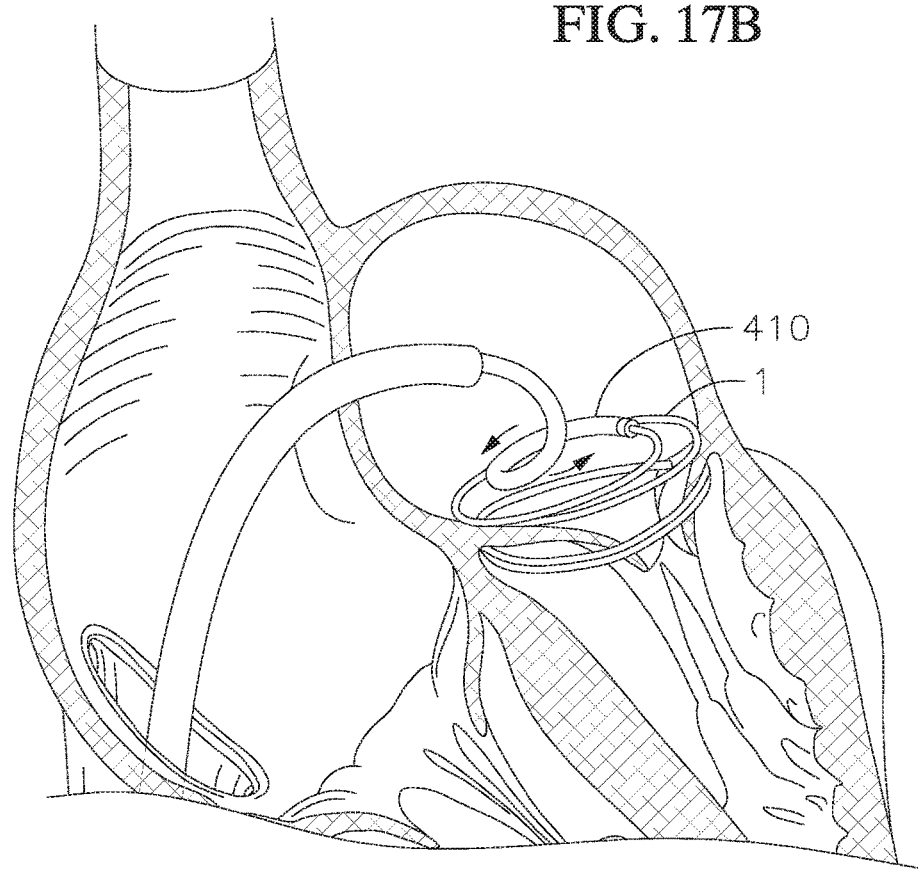

In FIGS. 17A and 17B, with the reference to the mitral valve, another method of retracting the delivery catheter is shown. While the knob 450 is held fixed, if appropriately configured, the handle body 440 of the pusher tool 430 (and the catheter handle 420 if one is present) can be rotated relative to the knob 450 in a direction opposite to the direction that the knob 450 was rotated, for example, in a counter-clockwise direction in the instant embodiment, causing the distal region of the delivery catheter 410 to also rotate in the same direction. The system and devices can be configured such that this rotational motion causes translational motion of the delivery catheter proximally to retract the delivery catheter from off the anchoring/docking device. Since the docking device 1 is held in place when the delivery catheter 410 is rotated, the delivery catheter 410 can be retracted relative to the docking device 1, thereby releasing the second portion or atrial turn(s) of the docking device 1 from the delivery catheter 410, without the docking device 1 advancing any further into the left ventricle or retracting back into the left atrium.

Figure 11:
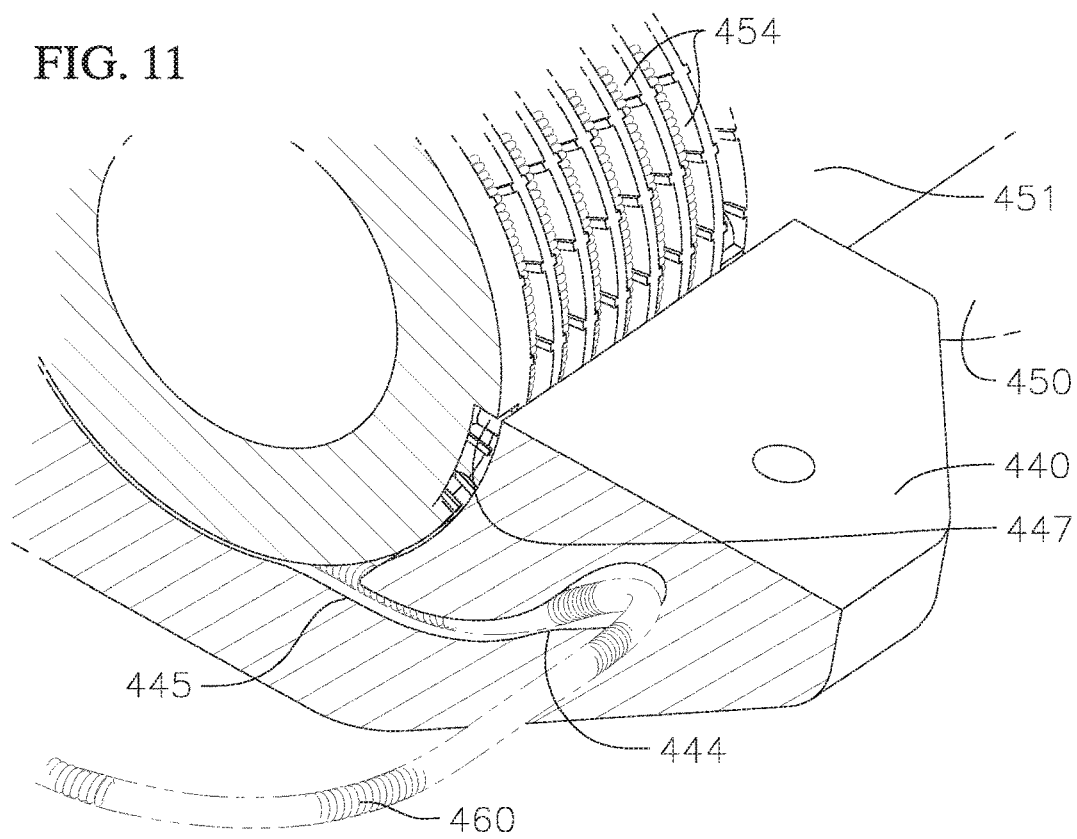
FIG. 11 shows an enlarged and partial cross-sectional view of a section of the pusher tool of FIGS. 9 and 10, including portions of the pusher wire and a pathway for advancing and retracting the pusher wire relative to the rest of the pusher tool.

The handle body 440 of the pusher tool 430 can also be rotated relative to the knob 450, which as best seen in FIGS. 10 and 11, will also result in release and further distal advancement of the pusher or pusher wire/tube 460 from the pusher tool 430. The amount of advancement of the pusher or pusher wire/tube 460 can correspond substantially to the length of the docking device 1 that is released into the left atrium, so that the pusher or pusher wire/tube 460 provides sufficient slack to replace the length of the docking device 1 that was held in the delivery catheter 410 prior to deployment of the atrial turns, to further facilitate holding of the docking device 1 in place during this process.

Connection of the docking device 1 to the pusher or pusher wire/tube 460 via the retrieval line 468 (e.g., a retrieval suture) can also facilitate pulling of the docking device 1, for example, to readjust or retrieve the docking device 1 from the implant site. Such retrieval is possible during any stage of delivery of the docking device 1, and can be accomplished in similar manner as deployment of the docking device 1. For example, if adjustment of the ventricular coils of the docking device 1 is desired, the position of the docking device 1 can be retracted or pulled backwards by rotating the knob 450 in the opposite direction to advancement, for example, counter-clockwise in this embodiment. In one embodiment, to hold the docking device 1 at the same position, while retracting a proximal portion (e.g., part of the stabilization coil/turn or atrial coil/turn) of the docking device 1 back into the delivery catheter 410, the handle body 440 of the pusher tool 430 or the knob can be rotated in the opposite direction to advancement (e.g., clockwise in this embodiment). Partial or full retrieval of the docking device into the delivery catheter is possible.

Once the docking device 1 has been delivered to a desired position, the retrieval line/suture 468 can be released, for example, with the locking knob 457 or the suture/line locking mechanism 470 (e.g., by cutting along slot/window/cut-out 469 to cut a portion of the suture), the docking device 1 can be separated from the pusher wire/tube 460, and the delivery device 400 can be removed from the implant site. The THV 80 can then be delivered to and expanded in the docking device 1 to complete the valve replacement procedure.

The delivery device 400 can be configured for delivering different shaped and oriented docking devices in other embodiments. For example, while the above example discusses clockwise advancement of the docking device 1, the docking device 1 can be adapted for delivering a coil anchor that is advanced counter-clockwise as well, for example, the docking device 1 shown in FIG. 3. In this arrangement, rotation of the respective parts would be in the opposite direction to the method discussed in FIGS. 16A to 17B. For example, the knob 450 would be rotated in a counter-clockwise direction to advance the docking device 1 out of the delivery catheter 410, while the knob would be rotated clockwise to retract the docking device 1 back into and/or further into the delivery catheter.

Figure 18:
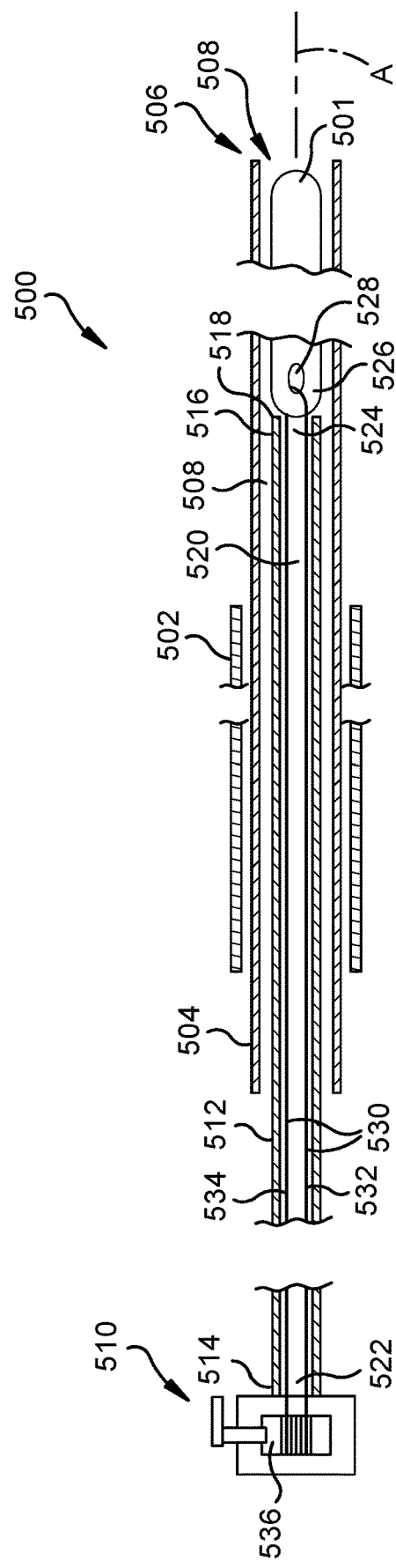
FIG. 18 shows a schematic representation of an exemplary system for delivering an anchoring or docking device, shown with the anchoring or docking device within a delivery catheter and engaging a pusher or a pusher wire or tube.
Figure 19:
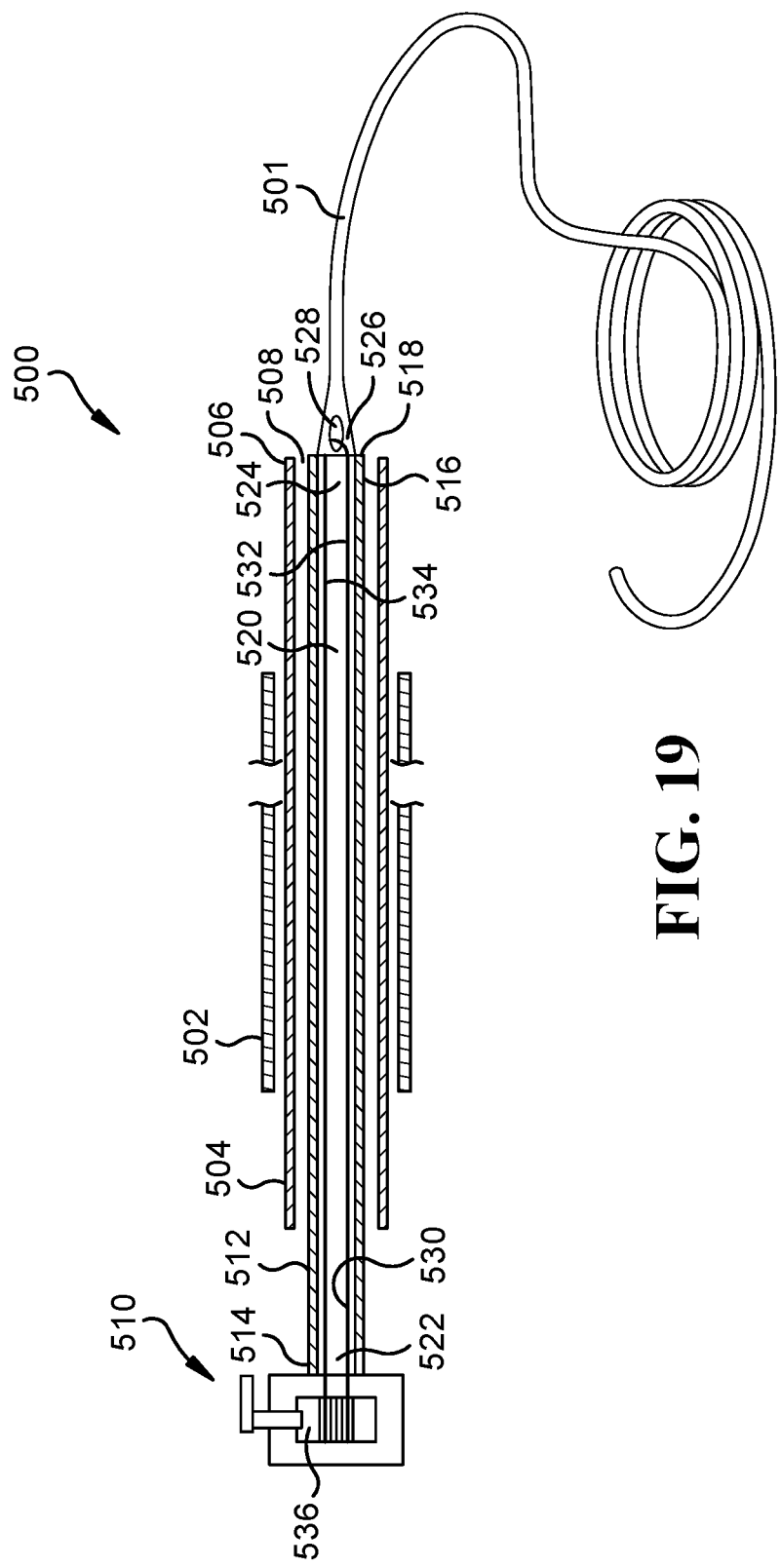
FIG. 19 shows a schematic representation of an exemplary system for delivering an anchoring or docking device, shown with the anchoring or docking device outside a delivery catheter and engaging a pusher or a pusher wire/tube.
Figure 20:
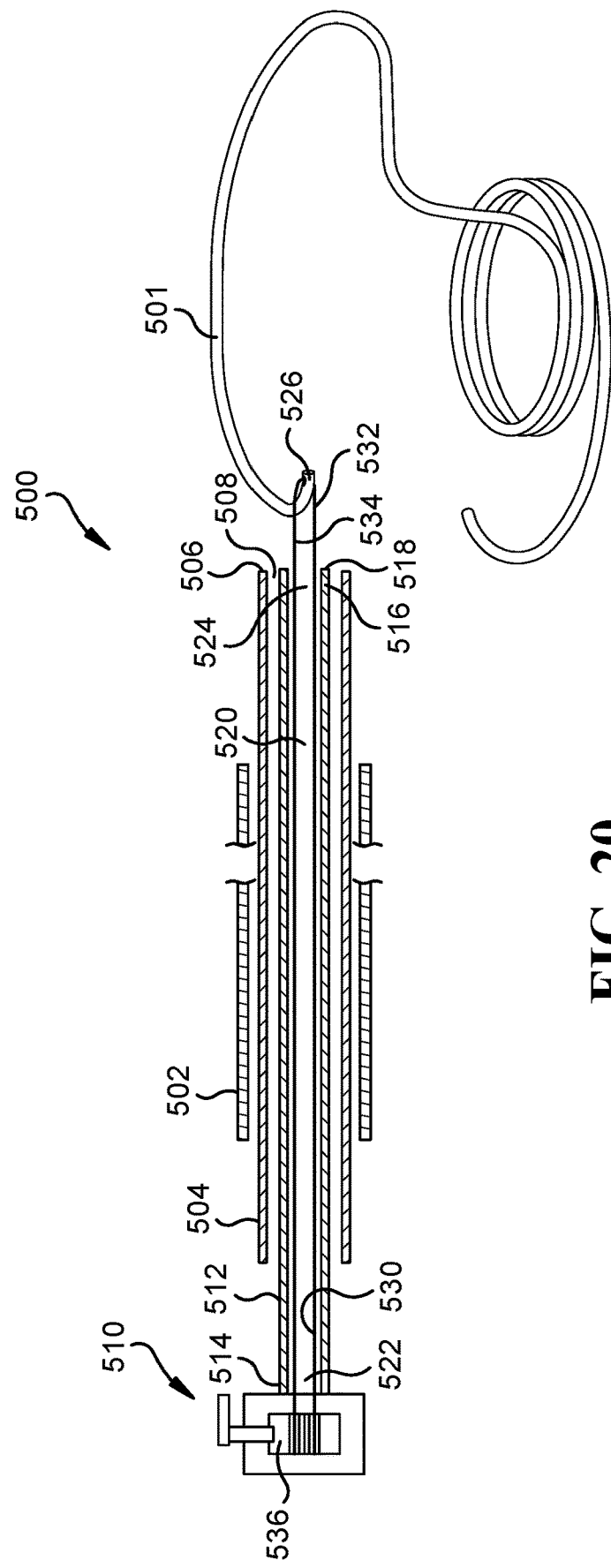
FIG. 20 shows a schematic representation of an exemplary embodiment of a system for delivering an anchoring or docking device, shown with the anchoring or docking device outside a delivery catheter and disengaged from the pusher wire or tube.

FIGS. 18-20 illustrate an exemplary embodiment of a system 500 (which can include the same or similar features/components as system 400) for delivering a docking device 501 to a native valve of a patient's heart. The system 500 includes a guide sheath 502 which houses and protects a delivery catheter 504, which can be similar to or the same as the sheath 480 and the delivery catheter 410, previously described. The delivery catheter 504 includes an open distal end 506 and central lumen 508. The system 500 also includes a pusher tool 510 and a pusher or pusher wire/tube 512, which can be the same as or similar to or the same as the pusher or pusher wire/tube 460, 460', previously described.

The pusher wire/tube 512 includes a proximal end 514 fixedly attached to the pusher tool 510 and a distal end 516 having a device abutment surface 518. The pusher wire/tube 512 can include a central lumen 520 extending through the pusher wire/tube 512 from the proximal end 514 to the distal end 516. The central lumen 520 can be open at the proximal end 514 via a proximal opening 522 and can be open at the distal end via a distal opening 524.

The docking device 501 can include a proximal end 526 having one or more holes 528 extending transversely through the proximal end 526. The system 500 can include a retrieval line/suture 530 that connects the docking device 501 to the pusher tool 510. The retrieval line/suture 530 can extend from the pusher tool 510, through the proximal opening 522, through the central lumen 520, out of the distal opening 524, through the hole 528 in the docking device 501 and return to the pusher tool 510 along the same path (e.g., forming a loop). Thus, the retrieval line/suture 530 can have a first leg 532 and a second leg 534 extending from the pusher tool 510 to the docking device 501.

The pusher tool 510 can include a suture/line locking mechanism the same as or similar to suture/line locking mechanism 470. For example, pusher tool 510 can include a rotatable member 536 (e.g., the same as or similar to rotatable member 473 of suture/line locking mechanism 470 or the rotatable member can take any other form), which the retrieval line/suture 530 may wind around. By rotating the rotatable member 536, the amount of the retrieval line/suture 530 that extends from the pusher tool 510 can be lengthened or shortened. As shown in FIG. 18, the rotatable member 536 can be rotated such that the retrieval line/suture 530 draws the proximal end 526 of the docking device 501 against the device abutment surface 518. In this position, the docking device 501 is held securely against the pusher wire/tube 512 such that the docking device 501 and the pusher wire/tube 512 move in unison. In this manner, movement of the pusher tool 510 relative to the delivery catheter 504 along the longitudinal axis A (FIG. 18) of the system 500 can move the docking device 501 within the central lumen 508 of the delivery catheter 504.

As shown in FIG. 19, the pusher tool 510 and the pusher wire/tube 512 can be advanced relative to the delivery catheter 504 such that the docking device 501 is advanced out of the central lumen 508 and past the open distal end 506 of the delivery catheter 504. The retrieval line/suture 530, however, remains in tension such that the proximal end 526 of the docking device 501 is held against the device abutment surface 518 of the pusher wire/tube 512.

As shown in FIG. 20, once the docking device 501 has been pushed out of the delivery catheter 504 by the pusher or pusher wire/tube 512, the pusher tool 510 can create slack in the retrieval line/suture 530 by allowing out additional length of the retrieval line/suture 530. When tension in the retrieval line/suture 530 has been removed, the proximal end 526 of the docking device 501 is no longer held in engagement with the device abutment surface 518 of the pusher wire/tube 512. During delivery, the docking device 501 can be held in the delivery catheter 504 in a relatively straight configuration for easier maneuverability through the delivery catheter 504. After exiting the delivery catheter 504 and tension in the retrieval line/suture 530 is removed, the docking device 501 can return to its original coiled or curved shape and placement of the docking device 501 can be completed.

Since, however, the retrieval line/suture 530 remains connected to the docking device 501, the docking device 501 can be retrieved or readjusted from the implant site by retracting the retrieval line/suture 530 back through the central lumen 520 of the pusher wire/tube 512 until the proximal end 526 of the docking device 501 is pulled into abutment with the device abutment surface 518 of the pusher wire/tube 512. The pusher wire/tube 512 can then be pulled back through the central lumen 508 of the delivery catheter 504 and, if necessary, the docking device 501 can be wholly or partially pulled into the delivery catheter 504 for removal or replacement.

If the docking device 501 is properly implanted, the docking device 501 can be disconnected from the retrieval line/suture 530, such as for example, by cutting or severing the retrieval line/suture 530 or a portion thereof. Once the docking device 501 is disconnected from the retrieval line/suture 530, the pusher tool 510 and retrieval line/suture 530 can be withdrawn, leaving the docking device 501 in place. For example, one end of the retrieval line/suture 530 may be cut at or near the rotatable member 536 (e.g., in a slot/window/cut-out the same as or similar to slot/window/cut-out 469). Once the end is cut, the rotatable member 536 can be rotated to draw the cut end down the pusher wire/tube 512 to the hole 528, through the hole 528, and back into the pusher wire/tube 512 to permanently release the docking device 501. In another embodiment, both or either of the ends of the retrieval line/suture 530 may be cut with either end being drawn through the hole 528 to release the docking device 501.

Figure 21:
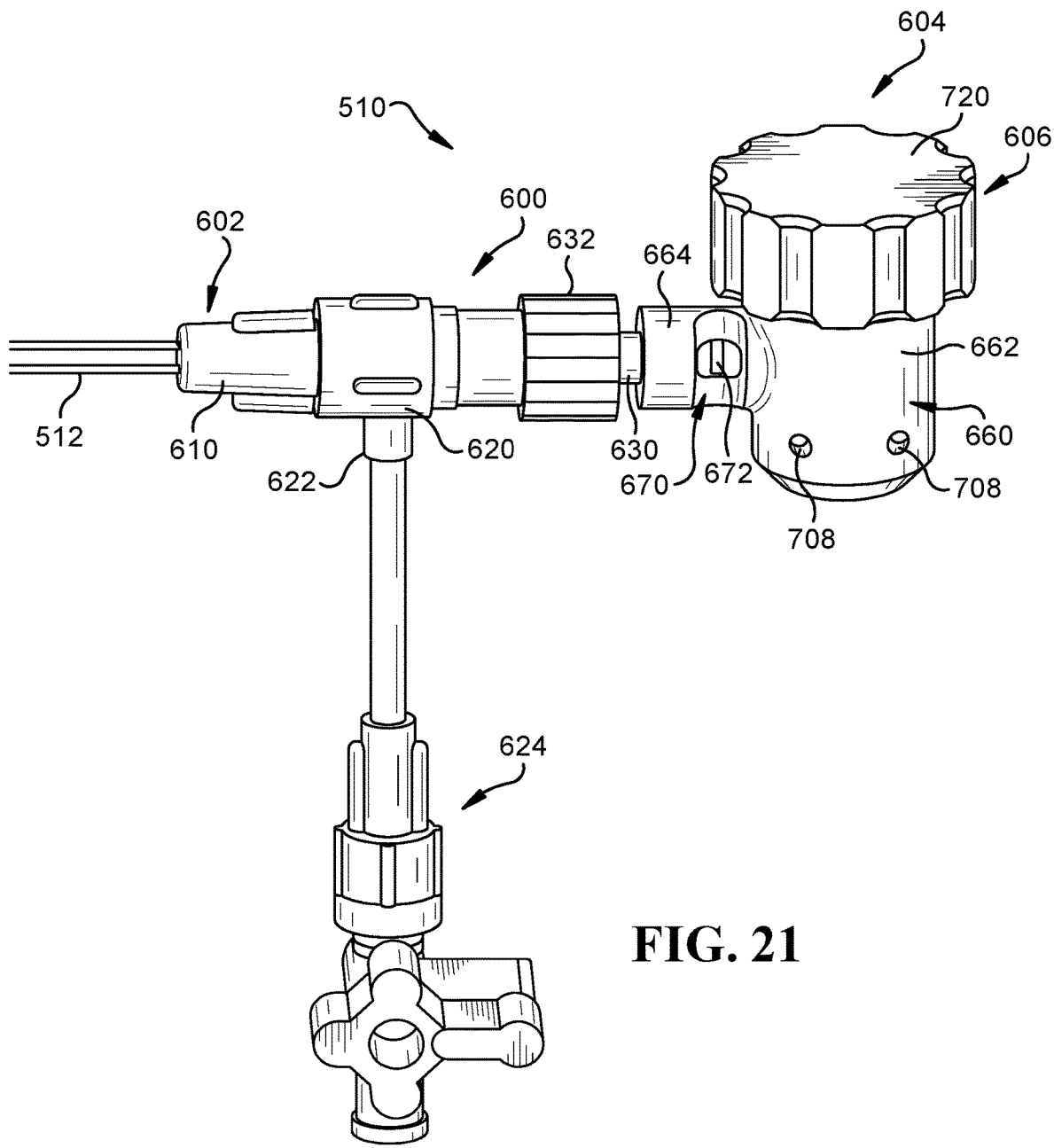
FIG. 21 shows a perspective view of an exemplary embodiment of a pusher tool that can be used in the system of FIGS. 18-20, including a suture/line lock or locking mechanism.
Figure 22:
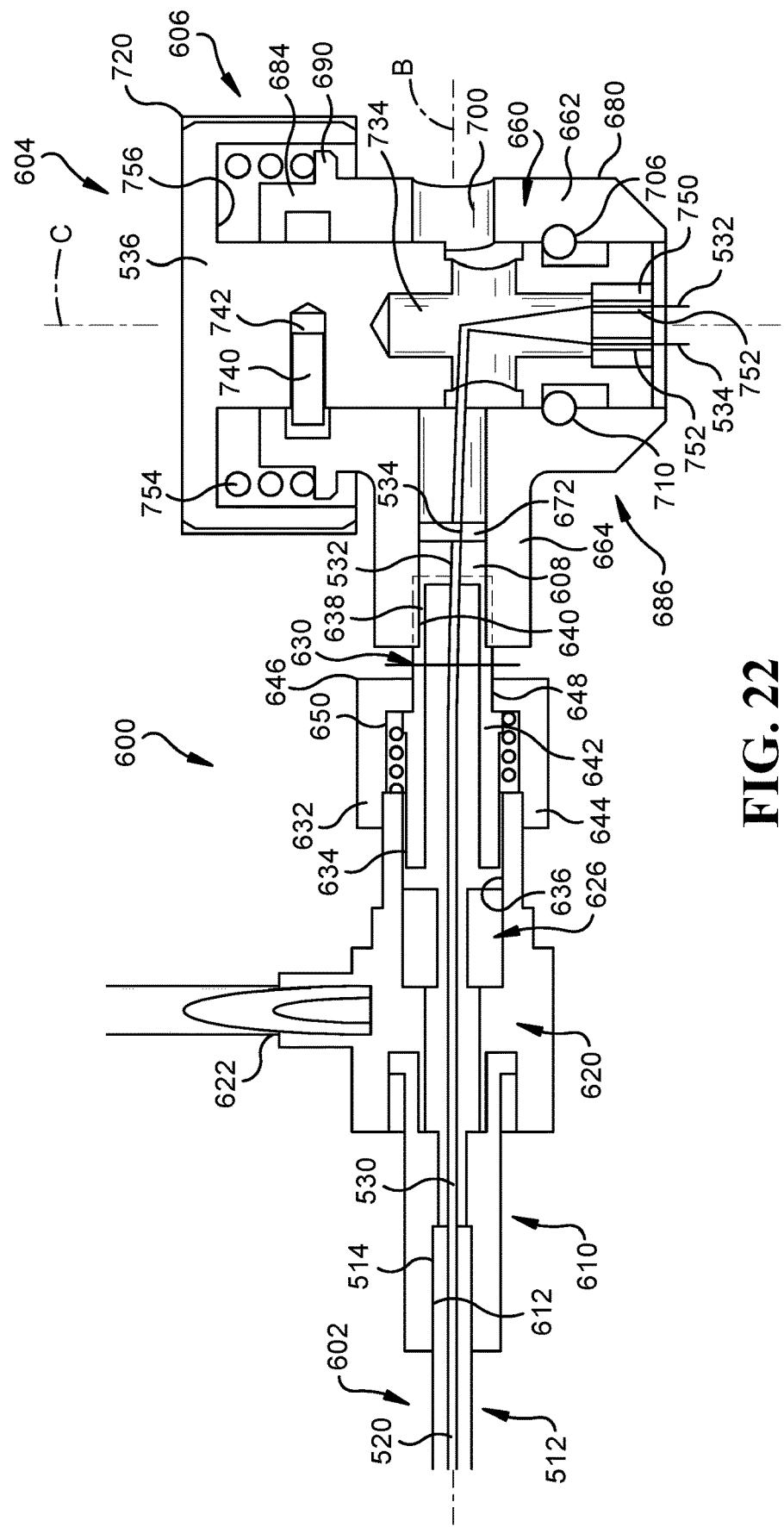
FIG. 22 is a side sectional view of the pusher tool of FIG. 21.

The pusher tool 510 can be configured in a variety of ways. Any tool capable of advancing the docking device 501 through the delivery catheter 504 while allowing controlled deployment and retrieval of the docking device 501 can be used. Referring to FIGS. 21 and 22, as shown in the illustrated exemplary embodiment, the pusher tool 510 includes a body 600 having a forward portion 602 adapted to receive and fixedly attach to the proximal end 514 of the pusher wire/tube 512 and a rearward portion 604 including a suture/line locking mechanism 606, which can be the same as or similar to the suture/line locking mechanism 470 described above. The body 600 can be generally elongated and can include a pathway 608 (FIG. 22) extending from the forward portion 602 to the suture/line locking mechanism 606. The body 600 and pathway 608 can be formed as a single unitary structure or can be formed from a plurality of attached components and fittings. The number and type of components and fittings can vary in different embodiments.

The forward portion 602 can fixedly attach to the proximal end 514 of the pusher or pusher wire/tube 512 in any suitable manner, such as a friction fit, a threaded connection, adhesives, fasteners, or other suitable connections. As shown in the illustrated embodiment, the forward portion 602 can include a first connector 610 having a bore 612 sized to closely receive the proximal end 514 of the pusher wire/tube 512 such that the central lumen 520 of the pusher wire/tube 512 can communicate with the pathway 608 in the body 600. As shown in the illustrated embodiment, the central lumen 520 can be coaxially aligned with the pathway 608 along an axis B (FIG. 22) of the pathway 608.

As shown in the illustrated exemplary embodiment, the first connector 610 can be attached to a flush fitting 620. The first connector 610 may attach to the flush fitting 620 by any suitable manner, such as a friction fit, a threaded connection, adhesives, fasteners, or other suitable connections. As shown in the illustrated embodiment, the flush fitting 620 can be a T-fitting having a flush port 622 in fluid communication with the pathway 608. The flush port 622 can be connected to or connectable to a flushing system 624 (FIG. 21) for introducing a flushing fluid, such as saline, for example, into the pathway 608. A sealing assembly 626 (FIG. 22) can be provided in the flush fitting 620, or otherwise between the flush fitting and the locking mechanism 606, to prevent flushing fluid from entering the locking mechanism 606.

The suture/line locking mechanism 606 can be attached to the rest of the body 600 of the pusher tool 510 in any suitable manner, such as a friction fit, a threaded connection, adhesives, fasteners, or other suitable connections. As shown in the illustrated embodiment, the suture/line locking mechanism 606 can be attached to the flush fitting 620 via a second connector 630 and a sealing cap 632. In one exemplary embodiment, the connector 630 and sealing cap 632 allow the suture/line locking mechanism 606 to swivel relative to the remainder of the body 600. The second connector 630 can include a distal end 634 that is received within a bore 636 of the flush fitting 620, a proximal end 638 that is received within a bore 640 on the suture/line locking mechanism 606, and a rearward facing shoulder 642 positioned between the distal end 634 and the proximal end 638.

The sealing cap 632 can include a first end 644 that threadably engages the flush fitting 620 and a second end 646 having a bore 648 which the second connector 630 extends through. The shoulder 642 can abut an inner surface 650 of the sealing cap 632 adjacent the bore 648 to attach the second connector 630 to the flush fitting 620. While the sealing cap 632 swivels, the distal end 634 presses against a gasket, which closes and seals the path of the retrieval line/suture 530.

Figure 24:
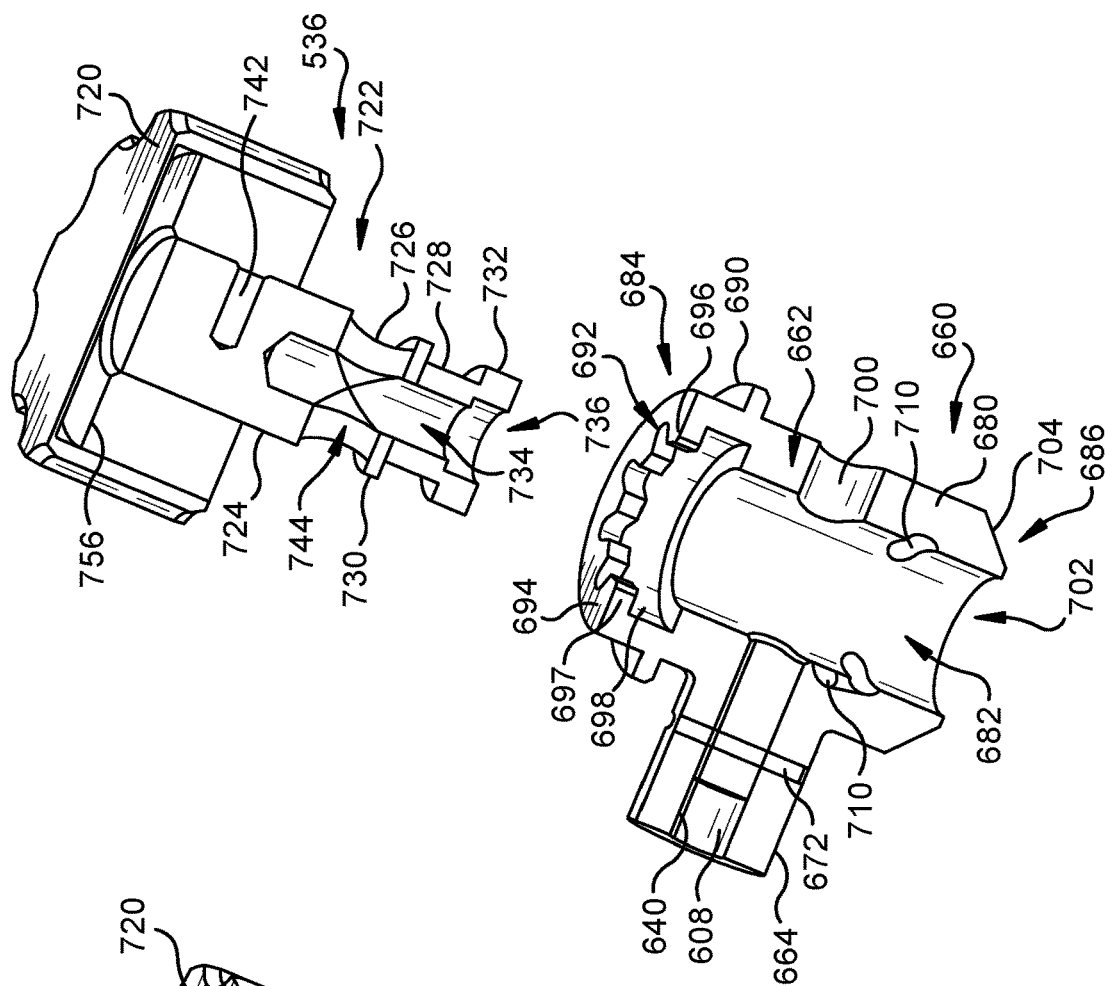
FIG. 24 is a sectional view of the rotatable member and a housing of FIG. 23.
Figure 23:
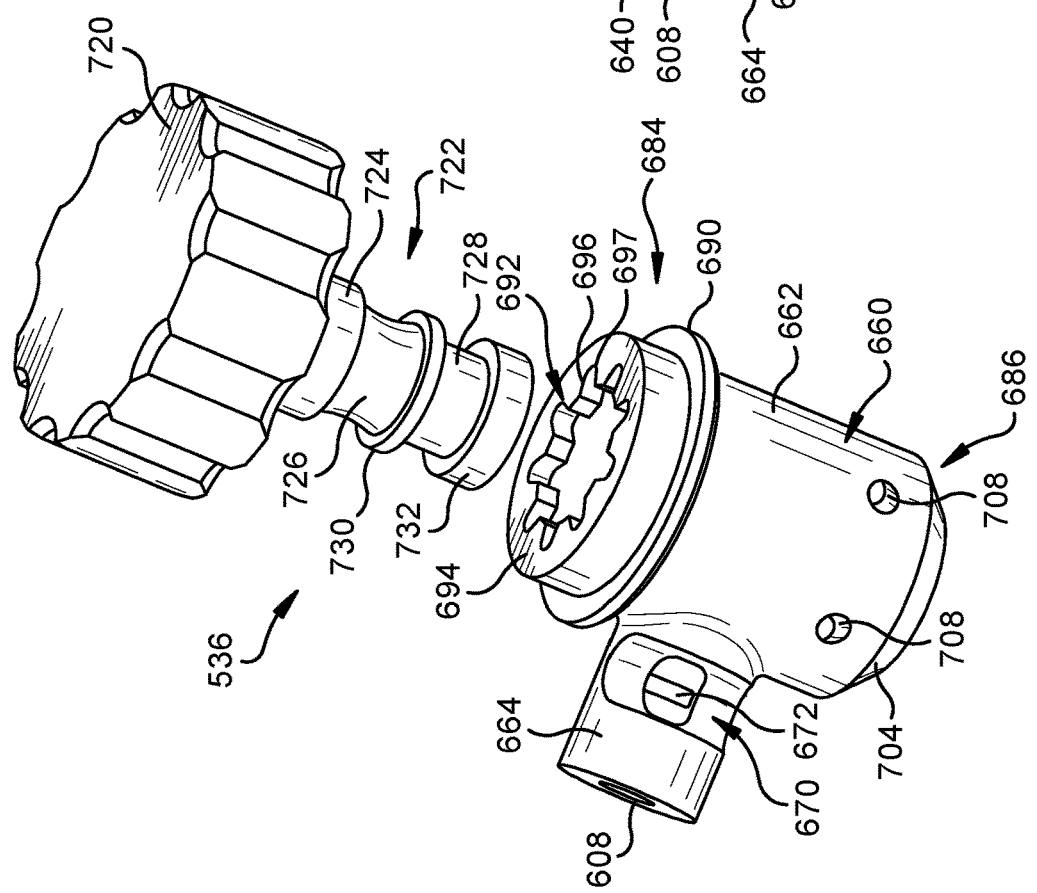
FIG. 23 is an exploded view a rotatable member and a housing of the suture/line lock or locking mechanism of FIG. 21.

The suture/line locking mechanism 606 can be configured in a variety of ways. Any mechanism capable of anchoring the retrieval line/suture 530, controlling the deployment and the retrieval of the retrieval line/suture 530, and locking the retrieval line/suture 530 at a set deployment can be used. Referring to FIGS. 23 and 24, in one embodiment, the suture/line locking mechanism 606 includes a body 660 (which can be generally T-shaped) having a first portion 662 and a second portion 664 that extends away from a central region of the first portion 662. The rotatable member 536 is received in the first portion 662 and rotatable about an axis C relative to the first portion 662 of the body 660.

The second portion 664 can include a bore 640 for receiving the proximal end 638 of the second connector 630. The bore 640 can extend the suture pathway 608 through the second portion 664 of the body 660 to the rotatable member 536 in the first portion 662 of the body 660.

The second portion 664 can include a slot, window, or cut-out 670 (e.g., the same as or similar to slot/window/cut-out 469) that provides access to the bore 640 from the exterior of the second portion 664. The slot/window/cut-out 670 can be configured in a variety of ways. For example, the location, the size, and the shape of the slot/window/cut-out 670 can vary for different embodiments. Any opening that provides access to the bore 640 such that a user may access the retrieval line/suture 530 within the bore 640 can be used. In the illustrated embodiment, the slot/window/cut-out 670 is formed as a semi-circular, vertical channel.

A divider 672 can be positioned within the bore 640 adjacent the slot/window/cut-out 670. The divider 672 can be configured in a variety of ways. Any structure that separates the two legs of the retrieval line/suture 530 within the bore 640 allowing one of the legs to be presented in the slot/window/cut-out 670 can be used. In the illustrated embodiment, the divider 672 is a dowel pin arranged vertically in the bore 640 and sized and positioned such that one leg of the retrieval line/suture 530 can pass on one side of the divider 672 and the other leg of the retrieval line/suture 530 can pass on the opposite side of the divider 672.

As shown in the illustrated embodiment, the first portion 662 can be formed by a generally cylindrical sidewall 680 defining a bore 682 extending from a first end 684 of the first portion 662 to a second end 686 opposite the first end 684. In some embodiments, however, the first portion 662 can be shaped other than cylindrical. The first portion 662 can include a radial lip 690 extending from the exterior of the cylindrical sidewall 680 proximate the first end 684.

The suture/line locking mechanism 606 can also include components or structure for locking the rotational position of the rotatable member 536 relative to the first portion 662. The components or structure can be configured in a variety of ways. Any components or structure capable of locking the rotational position of the rotatable member 536 relative to the first portion 662 can be used, such as for example, a splined connection. As shown in the illustrated embodiment, the first end 684 of the first portion 662 can include a gear-shaped first opening 692 in an end wall 694 of the first end 684. The first opening 692 can be axially aligned with the bore 682 along the axis C. The gear shape of the opening 692 can be formed by alternating radially extending projections 696 and recesses 697 spaced circumferentially around the first opening 692. As will be described in detail below, the projections 696 can act as stops that prevent rotation of the rotatable member 536. The number and size of the projections 696 and recesses 697 can vary in different embodiments. As shown in the illustrated embodiment, the gear shape of the opening 692 can be formed by nine alternating projections 696 and recesses 697. Each projection 696 and each recess 697 can be about 40 degrees apart from the next projection and recess, respectively.

The first end 684 can include a counter-bore 698 adjacent the first opening 692. The counter-bore 698 can be coaxially aligned with the bore 682 but can have a larger diameter than the bore 682. The first portion 662 of the suture/line locking mechanism 606 can also include a hole 700 that extends through the cylindrical sidewall 680 opposite and coaxial with the bore 640 of the second portion 664.

The second end 686 of the first portion 662 can include a second opening 702 opposite the first opening 692 and coaxial with the bore 682. The second opening 702 can have the same size and shape as the bore 682 or can have a different size and shape. As shown in the illustrated embodiment, the second end 686 can include a tapered or beveled exterior edge 704.

One or more stops 706 can be positioned between the hole 700 and the second opening 702 along the inner surface of the sidewall 680. The one or more stops 706 can be configured in a variety of ways, such as for example, the shape, size, and number of stops. Any structure capable of restricting axial movement of the rotatable member 536 can be used. As shown in the illustrated embodiment, the one or more stops 706 can include a pair of dowel pins. For example, the first portion 662 can include a pair of offset bores 708 (FIG. 23), each sized to receive one of the stops 706 and extending through the first portion 662 to form two recessed grooves 710 along an inner surface of the bore 682 opposite each other. When received in the offset bores 708, the stops 706 reduce the cross-sectional size of the bore 682 to create a choke-point.

The rotatable member 536 of the suture/line locking mechanism 606 can be configured in a variety of ways. Any configuration capable of engaging the retrieval line/suture 530 to deploy and retrieve the retrieval line/suture 530 can be used. For example, the rotatable member 536 can be configured such that manually rotating the rotatable member 536 winds or unwinds the retrieval line/suture 530 from around a portion of the rotatable member. As shown in the illustrated embodiment, the rotatable member 536 can include a handle 720 and a stem 722 extending from the handle 720. The handle 720 can be positioned at one end of the rotatable member 536 and extend outside of the first portion 662 of the T-shaped body 660. The handle 720 can be configured in a variety of ways. Any configuration that facilitates turning or rotating of the rotatable member 536 relative to the first portion 662 of the T-shaped body 660 can be used.

The stem 722 can be generally cylindrical and sized to be received within the bore 682 of the first portion 662. As shown in the illustrated embodiment, the stem 722 can include a proximal portion 724 adjacent the handle 720, a first reduced diameter portion 726 adjacent the proximal portion 724, a second reduced diameter portion 728 separated from the first reduced diameter portion 726 by a radial lip 730, and a distal end portion 732 adjacent the second reduced diameter portion 728. The stem 722 can include an inner passage 734 extending axially from the proximal portion 724 through the distal end portion 732 to form an opening 736 in the distal end portion 732.

The proximal portion 724 can include a radially extending projection 740 (FIG. 22). The projection 740 is configured to interact with the gear-shaped first opening 692. In particular, the projection 740 is sized to be received within one of the recesses 697 between two of the projections 696. The projection 740 can be configured in a variety of ways. For example, the projection 740 can be integrally formed with the stem 722 or can be a separate component that is attached, or otherwise connected, to the rotatable member 536. As shown in the exemplary embodiment, the stem 722 can include a radially extending bore 742 proximate the handle 720 that receives the projection 740 in the form of a dowel pin.

The first reduced diameter portion 726 can include a cross-bore 744 that communicates with the inner passage 734. In the illustrated embodiment, the cross-bore 744 extends through the first reduced diameter portion 726 generally perpendicular to the longitudinal axis C and has the same or similar diameter to the pathway 608. In some embodiments, however, the cross-bore 744 may be shaped, sized, and oriented differently.

As shown in FIG. 22, the rotatable member 536 can include an anchoring or engagement feature 750 for anchoring or holding one or more ends of the retrieval line/suture 530. The anchoring or engagement feature 750 can be configured in a variety of ways. Any feature capable of anchoring or holding one or more ends of the retrieval line/suture 530 can be used. As shown in the illustrated embodiment, the anchoring or engagement feature 750 can be cylindrical or generally cylindrical and can be sized to be received in the inner passage 734 at the distal end portion 732 of the rotatable member 536. The anchoring or engagement feature 750 can include a pair of passages 752 extending generally parallel to the inner passage 734. Each of the passages 752 can be sized to receive an end of the retrieval line/suture 530. In some embodiments, the anchoring or engagement feature 750 can include more or less than a pair of passages 752.

Referring to FIG. 22, when assembled, the stem 722 of the rotatable member 536 can be slidably and rotatably received within the bore 682 of the first portion 662 of the suture/line locking mechanism 606 and the handle 720 extends from the first end 684. The cross bore 744 of the rotatable member 536 can be in communication with the pathway 608 and the anchoring or engagement feature 750 can be positioned in the inner passage 734 at the distal end portion 732 of the rotatable member 536.

The first leg 532 and the second leg 534 of the retrieval line/suture 530 can extend from the docking device 501, through the pusher or pusher wire/tube 512, through the pathway 608, and into the rotatable member 536 via the cross-bore 744. From the cross-bore 744, the first leg 532 and the second leg 534 of the retrieval line/suture 530 can enter the inner passage 734 and extend along the inner passage 734 to the anchoring or engagement feature 750 at the distal end portion 732. At the anchoring or engagement feature 750, the first leg 532 of the retrieval line/suture 530 can extend through one of the pair of passages 752 and the second leg 534 of the retrieval line/suture 530 can extend through the other of the pair of passages 752. Once through the passages 752, the first leg 532 and the second leg 534 can be anchored in place, such as for example, by being tied together or knotted at their ends.

In one embodiment, as the first leg 532 and the second leg 534 of the retrieval line/suture 530 extend through the pathway 608 past the divider 672, the first leg 532 of the retrieval line/suture 530 passes along one side of the divider 672 and the second leg 534 passes along the opposite side of the divider 672 such that the divider 672 separates the two legs 532,534.

The stem 722 of the rotatable member 536 can be positioned within the bore 682 such that the second reduced diameter portion 728 is adjacent the recessed grooves 710 on the inner surface of the bore 682. The stops 706, when inserted in the recessed grooves 710, extend, at least partly, into the second reduced diameter portion 728 and between the radial lip 730 and the distal end portion 732 of the stem 722. Thus, axial movement of the rotatable stem 722 of the rotatable member 536 within the bore 682 can be limited by the stops 706.

The rotatable member 536 can be axially moveable within the bore 682 between a first position and a second position. The suture/line locking mechanism 606 can include a biasing member 754 that biases the rotatable member 536 to the first position. The biasing member 754 can be configured in a variety of ways. Any biasing member capable of biasing the rotatable member 536 to the first position can be used. As shown in the illustrated embodiment, the biasing member 754 can be a spring positioned between the radial lip 690 and an underside surface 756 of the handle 720 to bias the handle 720 away from the T-shaped body 660.

Figure 26:
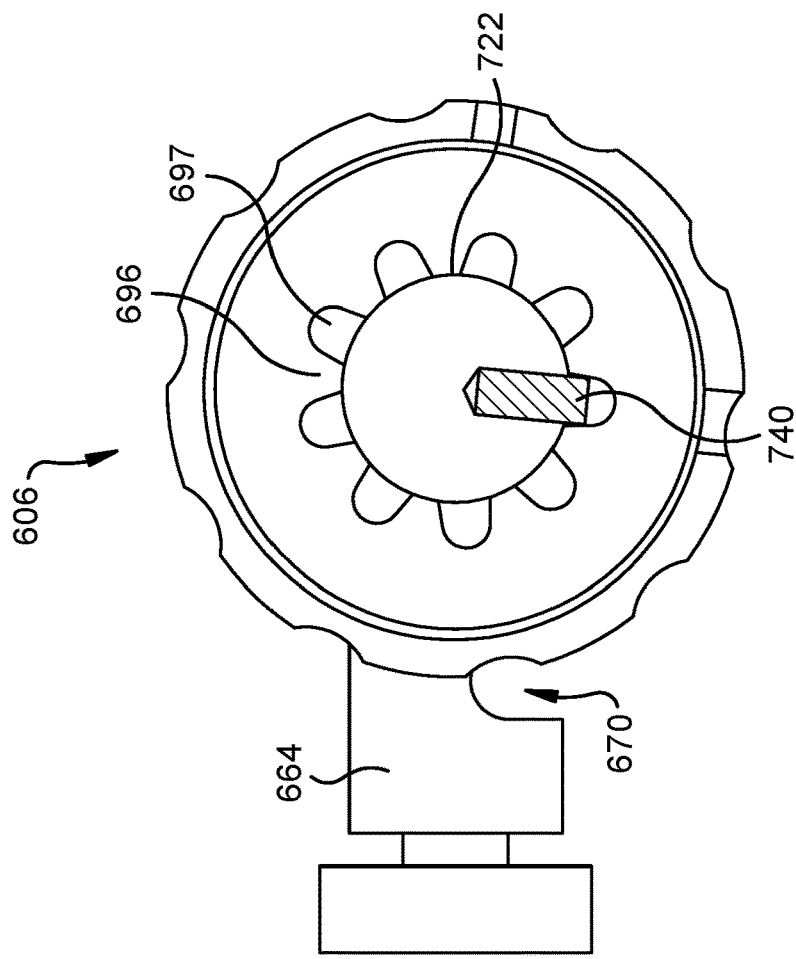
FIG. 26 is a top sectional view of the suture/line lock or locking mechanism of FIG. 25.
Figure 25:
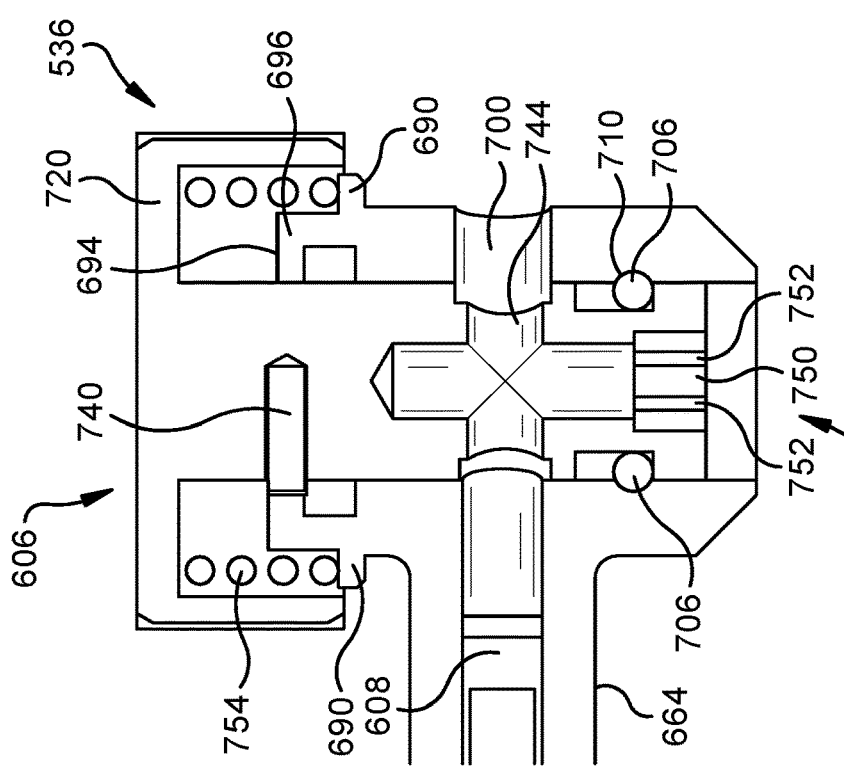
FIG. 25 is a side sectional view of an exemplary suture/line lock locking mechanism in a first position.

Referring to FIGS. 25 and 26, in the illustrated first position, the distal end portion 732 of the stem 722 engages the stops 706 to prevent further upward axial movement of the rotatable member 536. The cross-bore 744 is positioned to communicate with the pathway 608. In the illustrated embodiment, the cross-bore 744 is coaxially aligned with the pathway 608. In some embodiments, however, the cross-bore 744 need not be coaxially aligned with the pathway 608 in the first position.

At the proximal portion 724 of the stem 722, the projection 740 can be positioned in one of the plurality of recesses 697 between adjacent projections 696. Thus, the radially extending projections 696 can prevent rotation of the rotatable member 536 by engaging the projection 740. The first position, therefore, can be a locked position.

Figure 27:
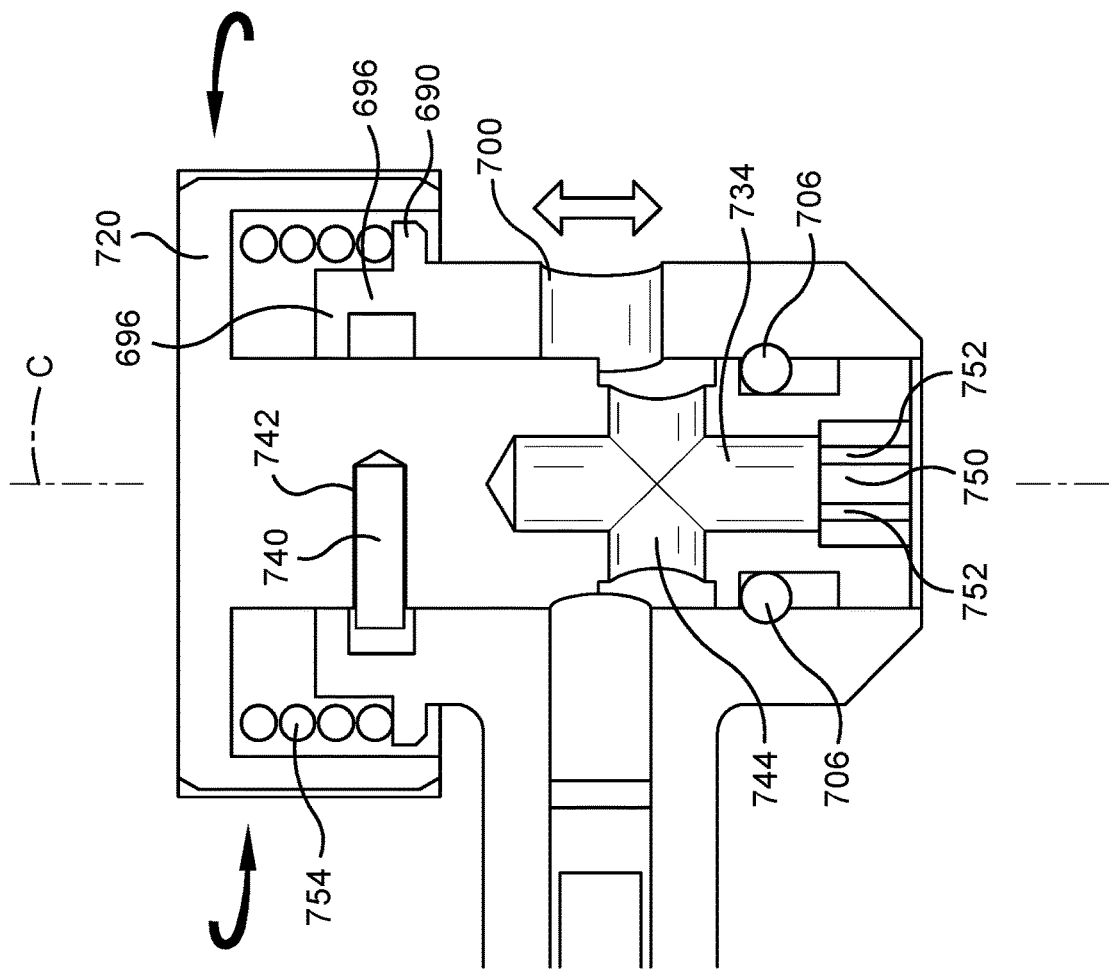
FIG. 27 is a side sectional view of the suture/line lock or locking mechanism of FIG. 25 in a second position.

Referring to FIG. 27, in the illustrated second position, the rotatable member 536 is moved downward relative to the T-shaped body 660 against the bias of the biasing member 754. The radial lip 730 engages the stops 706 to prevent further downward axial movement of the rotatable member 536. The cross-bore 744, while not aligned with the pathway 608, is still positioned to communicate with the pathway 608. At the proximal portion 724 of the stem 722, the projection 740 is positioned in the counter bore 698 of the first portion 662 below the plurality of recesses 697 and radially extending projections 696 of the first opening 692 (see FIGS. 23 and 24). Thus, the rotatable member 536 is able to rotate about the axis C. The second position, therefore, is a rotatable position.

In operation, a user can move the handle 720 to the second position, for example, by pushing it downward relative to the T-shaped body 660. In the second position, the rotatable member 536 can be rotated by the handle 720. Rotating the rotatable member 536 in a first direction, such as for example, clockwise, can wind a portion of the retrieval line/suture 530 around the first reduced diameter portion 726 of the stem 722; thus, retrieving or reducing the amount of retrieval line/suture 530 that extends from the suture/line locking mechanism 606. Rotating the rotatable member 536 in a second direction opposite the first direction, such as for example, counterclockwise, can unwind a portion of retrieval line/suture 530 from first reduced diameter portion 726 of the stem 722; thus, deploying or increasing the amount of retrieval line/suture 530 that extends from the suture/line locking mechanism 606. In one embodiment, to lock the amount of retrieval line/suture 530 that has been deployed, the user can release the handle 720 allowing the biasing member 754 to move the rotatable member 536 to the first position; thus preventing the rotatable member 536 from rotating. Locking the retrieval line/suture 530 by wrapping the retrieval line/suture 530 around the rotatable member 536 and preventing the rotatable member 536 is a friction locking method that reduces the risk of the retrieval line/suture 530 tearing when compared to locking methods which are based on clamping the retrieval line/suture 530, especially with thin retrieval lines/sutures.

To release the docking device 501 from the retrieval line/suture 530, the first leg 532, the second leg 534, or both legs of the retrieval line/suture 530 can be cut at the slot/window/cut-out 670 in the second portion 664 of the body 660. For example, in the illustrated embodiment, since the first leg 532 and the second leg 534 of the retrieval line/suture 530 are separated in the pathway 608 adjacent the slot/window/cut-out 670 by the divider 672, only a single leg is presented at the slot/window/cut-out 670, with the other leg being positioned behind the divider 672. The single leg in front of the divider 672, therefore, can be cut without concern for cutting the other leg. Once one of the first or the second leg 532, 534 is cut, the cut or severed end of the retrieval line/suture 530 can be pulled through the central lumen 520 toward the docking device 501, through the hole 528 in the docking device 501 to release the docking device 501, and back through the central lumen 520 of the pusher wire. This can be accomplished by in a number of ways. For example, the handle 720 can simply be pressed down and rotated to wind the retrieval line/suture 530 onto the stem 722. Or, the suture/line locking mechanism 606 can be disconnected from the pusher tool 510 by disconnecting the first end 644 of the sealing cap 632 from the flush fitting 620. Since the retrieval line/suture 530 is attached to the suture/line locking mechanism 606, removing the suture/line locking mechanism 606 from the rest of the pusher tool 510 will pull the retrieval line/suture 530 through the hole 528 and disconnects the docking device 501.

Optionally, the various pushers (e.g., pusher wires, pusher tubes, etc.) described herein can have a coating over and/or inside it, e.g., the pushers can have an interior lumen lined by PTFE to allow a line (e.g., a suture) to be atraumatically actuated through the lined lumen.

The various manipulations and controls of the systems and devices described above can be automated and/or motorized. For example, the controls or knobs described above can be buttons or electrical inputs that cause the actions described with respect to the controls/knobs above. This can be done by connecting (directly or indirectly) some or all of the moving parts to a motor (e.g., an electrical motor, pneumatic motor, hydraulic motor, etc.) that is actuated by the buttons or electrical inputs. For example, the motor can be configured, when actuated, to cause the control wires or pull wires described herein to tension or relax to move the distal region of the catheter. Additionally or alternatively, the motor could be configured, when actuated, to cause the pusher to move translationally or axially relative to the catheter to cause an anchoring or docking device to move within and/or into or out of the catheter. Automatic stops or preventative measures could be built in to prevent damage to the system/device and/or patient, e.g., to prevent movement of a component beyond a certain point.

Additional systems, devices, components, methods, etc. are described in U.S. Provisional Patent Application Ser. No. 62/435,563, filed on Dec. 16, 2016, and titled "DEPLOYMENT TOOLS AND METHODS FOR DELIVERING AN ANCHORING DEVICE FOR A PROSTHETIC VALVE AT A NATIVE VALVE ANNULUS" and the related PCT Patent Application Serial No. PCT/US2017/066854 titled "DEPLOYMENT SYSTEMS, TOOLS, AND METHODS FOR DELIVERING AN ANCHORING DEVICE FOR A PROSTHETIC VALVE" filed on Dec. 15, 2017, each of which are incorporated by reference herein, and the systems, devices, components, methods, etc. can be integrated or used with the systems, devices, methods, etc. described herein mutatis mutandis.

In various other embodiments, any or all of the different features/components from the different embodiments discussed above can be combined or modified, based for example, on the shape and configuration of the docking device to be delivered and/or on the anatomy or needs of each individual patient. Features/components described with respect to one embodiment can be included in other embodiments even if not described with respect to that embodiment. Similarly steps described with respect to one method can be included in other methods even if not described with respect to that method. Steps described at various points in the disclosure, even if separated from each other, can be combined.

Furthermore, while only transseptal delivery of the docking device 501 has been discussed in detail, the tools and methods can be modified in other embodiments for other delivery procedures, for example, transatrial or transapical delivery. In addition, as has been discussed, while embodiments of the docking device 501 and delivery devices have generally been discussed above with respect to valve replacement at the mitral position, similar docking devices and delivery methods can also be applied at other valve sites as well, for example, at the tricuspid, pulmonary, or aortic valve positions. Docking devices similar to or the same as those discussed above, when applied to valves other than the mitral valve, can also provide a more secure landing zone for THVs at those sites as well.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather the scope of the disclosure is defined by the following claims.

What is claimed is:

1. A delivery device for delivering a docking device to a native valve annulus of a patient's heart, the delivery device comprising:
   a delivery catheter having a first lumen;
   and a pusher tool comprising: a pusher slidably received within the first lumen, the pusher having a distal portion, a proximal portion, and a second lumen extending from the proximal portion to the distal portion;
   a locking mechanism fixedly attached to the proximal portion of the pusher;
   and a retrieval line extending through the second lumen from the locking mechanism to the docking device to connect the docking device to the pusher tool;
   wherein the locking mechanism includes a rotatable member that engages the retrieval line, the rotatable member having a first position that locks the amount of retrieval line that extends from the locking mechanism and a second position that allows the amount of retrieval line that extends from the locking mechanism to be increased or decreased.

2. The delivery device of claim 1, wherein a portion of the retrieval line winds around the rotatable member.

3. The delivery device of claim 1, wherein the locking mechanism prevents the rotatable member from rotating when the rotatable member is in the first position.

4. The delivery device of claim 3, when the rotatable member is axially moveable between the first position and the second position.

5. The delivery device of claim 3, wherein the locking mechanism allows the rotatable member to rotate when the rotatable member is in the second position.

6. The delivery device of claim 3, wherein the locking mechanism includes a projection extending radially from the rotatable member, wherein the projection is configured to engage a stop surface defined by a body of the pusher tool to prevent rotation of the rotatable member.

7. The delivery device of claim 6, wherein the body includes a plurality of stops surfaces positioned circumferentially around the rotatable member.

8. The delivery device of claim 1, further comprising an anchor positioned within the pusher tool and configured to secure an end of the retrieval line.

9. The delivery device of claim 8, wherein the rotatable member comprises a first passage extending along a rotational axis of the rotatable member and wherein the anchor is positioned in the first passage.

10. The delivery device of claim 9, wherein the rotatable member comprises a handle and a second passage that intersects the first passage between the handle and the anchor.

11. A method of delivering a docking device to a native valve of a patient's heart, the method comprising:
    connecting the docking device to a pusher tool with a line, positioning the docking device and the pusher tool within a delivery catheter;
    positioning a distal region of the delivery catheter in an atrium of the heart;
    advancing a pusher of the pusher tool distally through the delivery catheter, wherein the pusher pushes the docking device in a first lumen of the delivery catheter;
    engaging the line with a rotatable member of the pusher tool;
    and rotating the rotatable member of the pusher tool to change the amount of the line extending from the pusher tool.

12. The method of claim 11, wherein rotating the rotatable member further comprises winding a portion of the line around the rotatable member.

13. The method of claim 11, further comprising anchoring the line to the rotatable member.

14. The method of claim 11, further comprising preventing the rotatable member from rotating when the rotatable member is in a first position.

15. The method of claim 14, further comprising allowing the rotatable member to rotate when the rotatable member is in a second position.

16. The method of claim 15, further comprising moving the rotatable member axially between the first position and the second position.

17. The method of claim 16, wherein moving the rotatable member axially further comprises depressing the rotatable member to move the rotatable member to the second position.

18. The method of claim 16, wherein moving the rotatable member axially further comprises biasing the rotatable member to the first position.

19. The method of claim 11, further comprising cutting the line to disconnect the docking device from the pusher tool.

20. The method of claim 16, wherein cutting the line further comprising cutting the line at a location between a distal end of the pusher and the rotatable member.

21. The method of claim 11, wherein the positioning of the docking device and the pusher tool within the delivery catheter further comprises positioning a sleeve within the first lumen of the delivery catheter and positioning at least a portion of the docking device within a second lumen of the sleeve.

22. The method of claim 21, wherein the docking device is entirely positioned within the second lumen of the sleeve.

23. The method device of claim 21, wherein the advancing of the pusher of the pusher tool distally through the delivery catheter further comprises pushing the sleeve with the pusher such that the pusher pushes the docking device and the surrounding sleeve in the first lumen of the delivery catheter.

24. The method of claim 21, further comprising removing the sleeve from the docking device by pulling proximally on the sleeve while holding the pusher tool in place.

* * * * *